(12) United States Patent
Guevremont et al.

(10) Patent No.: US 7,135,674 B2
(45) Date of Patent: *Nov. 14, 2006

(54) METHOD AND APPARATUS FOR FAIMS WITH A LASER-BASED IONIZATION SOURCE

(75) Inventors: Roger Guevremont, Ottawa (CA); Ragnar Dworschak, Ottawa (CA); Richard A. Yost, Gainesville, FL (US); Christopher Karl Hilton, Gainesville, FL (US); Michael William Belford, Santa Clara, CA (US)

(73) Assignees: Thermo Finnigan LLC, San Jose, CA (US); University of Florida, Gainesville, FL (US)

( * ) Notice: Subject to any disclaimer, the term of this patent is extended or adjusted under 35 U.S.C. 154(b) by 16 days.

This patent is subject to a terminal disclaimer.

(21) Appl. No.: 11/038,144

(22) Filed: Jan. 21, 2005

(65) Prior Publication Data
US 2005/0161597 A1    Jul. 28, 2005

Related U.S. Application Data

(60) Provisional application No. 60/537,881, filed on Jan. 22, 2004.

(51) Int. Cl.
*B01D 59/44* (2006.01)
*H01J 49/40* (2006.01)
(52) U.S. Cl. .................. 250/288; 250/281; 250/282; 250/286; 250/290

(58) Field of Classification Search ................ None
See application file for complete search history.

(56) References Cited

U.S. PATENT DOCUMENTS

| | | | |
|---|---|---|---|
| 5,420,424 A | 5/1995 | Carnahan et al. | |
| 6,495,823 B1 | 12/2002 | Miller et al. | |
| 6,504,149 B1 | 1/2003 | Guevremont et al. | |
| 6,621,077 B1 | 9/2003 | Guevremont et al. | |
| 6,653,627 B1 * | 11/2003 | Guevremont et al. | 250/288 |
| 6,690,004 B1 | 2/2004 | Miller et al. | |
| 6,787,765 B1 | 9/2004 | Guevremont et al. | |
| 2005/0161598 A1 * | 7/2005 | Guevremont et al. | 250/294 |

* cited by examiner

*Primary Examiner*—Nikita Wells
(74) *Attorney, Agent, or Firm*—Kenyon & Kenyon LLP

(57) ABSTRACT

A method of separating ions comprises applying a spot of a sample material to a target plate. The target plate is mounted in fluid communication with an ion inlet orifice of a FAIMS analyzer region and externally to the FAIMS analyzer region. Using a laser light source that is disposed external to the FAIMS analyzer region, the target plate is irradiated with light of a predetermined wavelength, the light of a predetermined wavelength being selected to affect the sample material applied to the target plate so as to produce ions of the sample material. The ions of the sample material are directed along an ion flow path between the target plate and FAIMS analyzer region, via the ion inlet orifice. A flow of a gas is directed counter-current to the ion flow path and passing through the target plate. The flow of gas through the target plate assists in desolvation of ions and directs neutral molecules away from the FAIMS analyzer region.

32 Claims, 13 Drawing Sheets

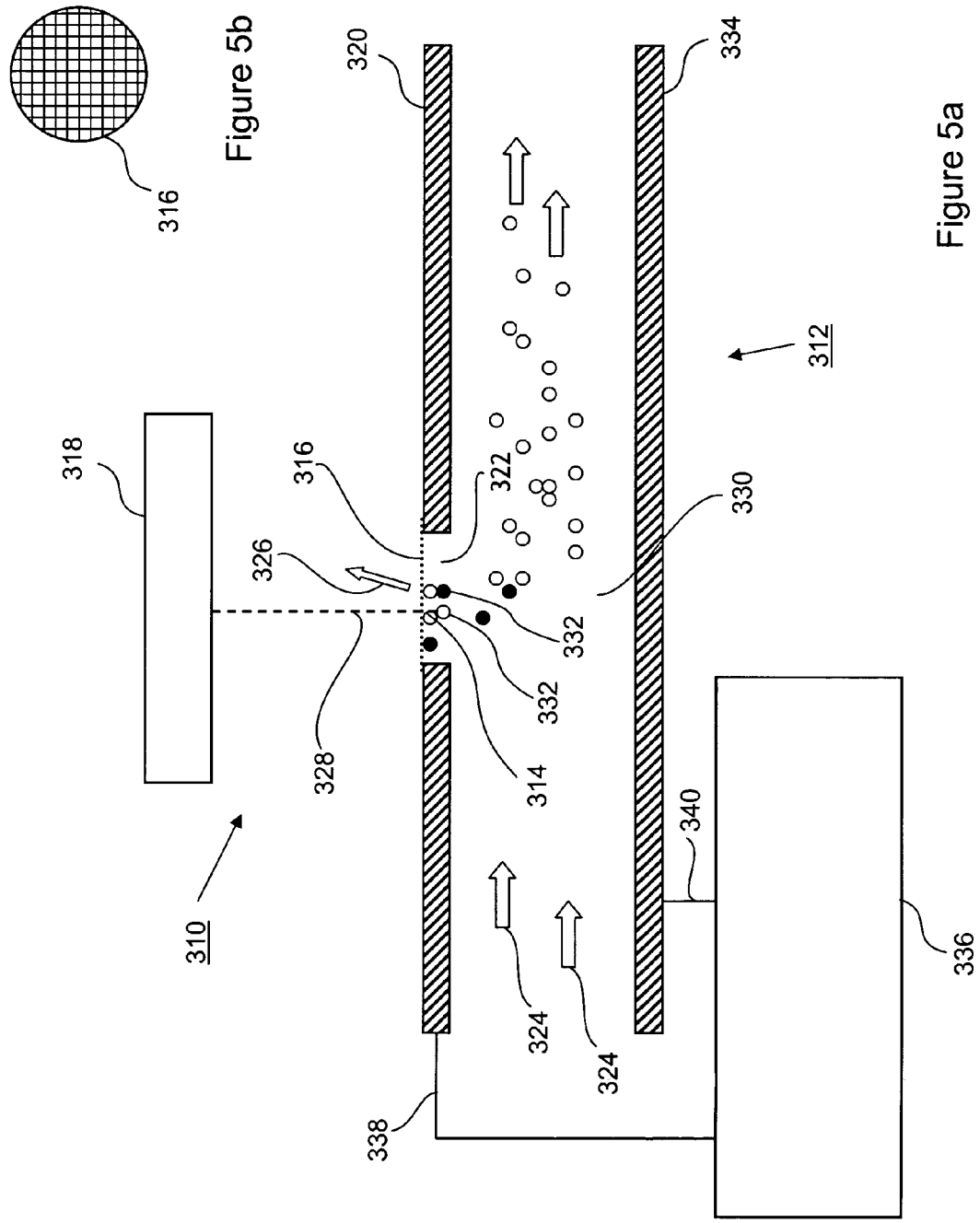

METHOD AND APPARATUS FOR FAIMS WITH A LASER-BASED IONIZATION SOURCE

This application claims benefit from U.S. Provisional Application No. 60/537,881 filed Jan. 22, 2004.

FIELD OF THE INVENTION

The instant invention relates generally to High-Field Asymmetric Waveform Ion Mobility Spectrometry (FAIMS), and more particularly to FAIMS with a laser-based ionization source.

BACKGROUND OF THE INVENTION

Biochemical and pharmaceutical applications have requirements for rapid screening and detection of compounds in extremely complex mixtures. Advances in chemical analysis technology applied to these fields must achieve a high degree of specificity in separations and incorporate systems that avoid slow separations, especially those involving chromatography and electrophoresis.

At present, the compounds in complex mixtures are separated and analyzed by chromatographic and electrophoretic methods combined with atmospheric pressure ionization-mass spectrometry (API-MS). In these separation techniques, a portion of a sample is introduced as a discrete pulse into the sample inlet of the API-MS system. The sample components are separated either through a component-specific interaction with mobile or stationary phases, or by differences in the drift velocities of components under the influence of electric fields. Because of the time that it takes for the components to migrate, chromatographic and electrophoretic methods require relatively long time periods to accomplish the separation, on the order of several minutes, whereas analysis by mass spectrometric methods provides data almost immediately. In practice, therefore, the mass spectrometer spends significant periods of time waiting for the arrival of transient signals. This is inefficient since the separation technology is very much less expensive than the MS instrumentation.

The above-mentioned problem is reduced when the separation technology operates in a continuous mode, for example the mixture is continuously delivered to the inlet of the separator and the selection of the separated components is electronically controlled. In this manner the MS acquires measurements of selected components in the mixture at almost full efficiency. Optionally, the MS is used to continuously study a particular component in a mixture until sufficient information is acquired. As will be obvious to one of ordinary skill in the art, operation of the separation technology in a continuous mode is impossible using existing chromatographic and electrophoretic techniques because the component of interest arrives only as a transient at the end of the separation. This transient mode of operation limits significantly the number and types of experiments that can be conducted during the lifetime of a given transient signal. Furthermore, if the information that is acquired during the transient is insufficient, a new sample must be injected and a delay is encountered during which the components are being separated.

Alternatively, complex mixtures may be studied using tandem mass spectrometry (MS/MS). With this technology, the ions are selected by a first mass analyzer operating at low pressure (e.g., $1 \times 10^{-5}$ torr) inside the vacuum chamber of a mass spectrometer, and are directed to enter a gas cell which is held at a higher bath gas pressure (e.g., $1 \times 10^{-3}$ torr). Upon entering this chamber, the ions collide with the molecules of bath gas and, if the kinetic energy of the ion is sufficient, the ion dissociates into some compound-specific fragments. The fragments pass out of the higher-pressure gas cell and are analyzed using a second mass analyzer, operating at a lower pressure, similar to that of the first mass analyzer. The advantage of tandem mass spectrometry is that the specificity is exceedingly high because of compound-specific fragmentation patterns that are created during the collision-induced dissociation. However, tandem MS requires considerable method development time and the operator must have expertise to operate the instrument. Furthermore, tandem MS cannot effectively quantify many kinds of isomeric ions (e.g., leucine and isoleucine) when both components coexist in the mixture. Accordingly, tandem MS is most suited to applications based on target compound analysis, where the system is used to search for a series of expected compounds and the identity of the expected fragment ions is known. Under these conditions the MS/MS experiment is capable of detecting ions at exceedingly low abundance, even in the presence of interfering compounds, since the MS/MS spectrum is very compound-specific. Tandem MS is less effective when used to study mixtures containing unknown components at trace concentrations. Since the existence of these unknowns cannot be predicted, the mass spectrum of the mixture must have peaks which are discernible above the background noise. In particular, detection of low intensity ions is a problem when using the electrospray ionization (ESI) technique, since ESI produces background ions that elevate the baseline intensity along the mass-to-charge ratio axis of a mass spectrum. This background of ions makes detection of unknown trace components difficult, if not impossible.

Of course, complex mixtures may also be analyzed using mass spectrometers with extremely high resolution, such as FT-ICR systems. However, high resolution mass spectrometers are very expensive.

FAIMS is a relatively new separation technique, which solves a number of the problems that are associated with the above-mentioned prior art techniques. FAIMS separates ions on a continuous basis, with the separation occurring under electronic control. Additionally, FAIMS reduces the background chemical noise inherent to atmospheric pressure ionization techniques, thus reducing the detection limits for unknown components in complex mixtures. Finally, FAIMS optionally is operated in tandem with many of the other technologies that are noted above, because the FAIMS device is located between the ion source and the mass spectrometer. A consequence of this physical location is that the FAIMS apparatus can be operated in conjunction with chromatography, electrophoresis, tandem mass spectrometry and high resolution mass spectrometry, etc.

Typically, ions are introduced into a FAIMS device after being formed by atmospheric pressure ionization, such as for instance corona discharge ionization, ionization by radioactive Ni, and electrospray ionization as just a few non-limiting examples. In each of these cases, the sample is one of a liquid and a gas, and in every case the analyte ions are suspended in a gas. One notable exception is found in U.S. Pat. No. 6,653,627, issued on Nov. 25, 2003 in the name of Guevremont et al., which discloses a FAIMS apparatus and method using a laser based ionization source. The entire contents of U.S. Pat. No. 6,653,627 are incorporated herein by reference. In that case, a matrix-supported sample is deposited on a target surface that is disposed within the FAIMS analyzer region, and irradiation is performed using a laser that is disposed external to the FAIMS analyzer region. Since ions are formed within the analyzer region, problems associated with low ion transmission efficiency through an ion inlet are eliminated. Unfortunately, in order to introduce new sample it is necessary to disassemble the FAIMS electrode assembly, remove the existing target surfaces, prepare new target surfaces, introduce the new target surfaces, and finally reassemble the FAIMS electrode assembly. Of course, this sample introduction technique does not support rapid screening of samples, and is very time consuming.

Placing the target surface of the laser source at a location that is external to the FAIMS analyzer would reduce the time and labor that is required for introducing new samples into the FAIMS. In order to achieve high ion transmission efficiency into the FAIMS analyzer region, the target surface should be located as close as possible to the ion inlet orifice of the FAIMS, and should also be disposed parallel to the ion inlet orifice. Unfortunately, when the target surface is disposed for achieving high ion transmission efficiency, very little space remains for arranging the laser light source at a position for irradiating the target surface.

It would be advantageous to provide a method and an apparatus for introducing ions, that are formed using a laser source, through an inlet into a FAIMS analyzer region, with high ion transmission efficiency. It would be further advantageous to provide a method and an apparatus for introducing such ions in a manner that supports rapid screening of samples.

SUMMARY OF THE INVENTION

It is an object of at least some of the embodiments of the instant invention to provide a method and an apparatus that overcomes at least some of the above-mentioned limitations of the prior art.

It is also an object of at least some of the embodiments of the instant invention to provide a method and an apparatus for introducing into the analyzer region of FAIMS, analyte ions from solid samples or from samples containing large biological or polymeric molecules.

It is also an object of at least some of the embodiments of the instant invention to provide a method and an apparatus for introducing analyte ions from sample compounds, in a manner that supports rapid screening of samples.

According to an aspect of the instant invention, provided is an apparatus comprising: a FAIMS analyzer for separating ions of a sample material and comprising an electrode having a first side and a second side that is opposite the first side, the first side of the electrode defining a boundary of a first region and the second side of the electrode defining a boundary of a second region; a gas inlet for providing a flow of a gas within the first region; an orifice having a periphery and being defined within a portion of the electrode for providing fluid communication between the first region and the second region; and, a laser-based ionization source for producing the ions of a sample material and comprising: a target plate disposed adjacent to the second side of the electrode and in an aligned relationship with the orifice, the target plate having a front surface for supporting the sample material thereon and having a back surface opposite the front surface, the target plate disposed for supporting a flow of the gas, via the orifice, in a direction from the first region to the second region; and, a laser light source in optical communication with the target plate for irradiating the sample material supported thereon with light of a predetermined wavelength, for producing the ions from the sample material.

According to another aspect of the instant invention, provided is an apparatus comprising: a FAIMS analyzer comprising a first electrode and a second electrode that is disposed in a spaced-apart relationship with the first electrode, a space between the first electrode and the second electrode defining a FAIMS analyzer region for separating ions of a sample material; an ion inlet orifice having a periphery and being defined within the first electrode; and, a laser-based ionization source for producing ions from a sample material and comprising: a target plate disposed adjacent to the ion inlet orifice and having a thickness, the target plate having a front surface for supporting the sample material thereon and having a back surface opposite the front surface, the target plate disposed for supporting a flow of a gas therethrough outwardly from the FAIMS analyzer region via the ion inlet orifice; and, a laser light source disposed external to the FAIMS analyzer region and in optical communication with the target plate for irradiating the sample material supported on the target plate with light of a predetermined wavelength, for producing the ions from the sample material.

According to still another aspect of the instant invention, provided is a method of separating ions, comprising: applying a spot of a sample material to a target plate; mounting the target plate in fluid communication with an ion inlet orifice of a FAIMS analyzer region and externally to the FAIMS analyzer region; using a laser light source that is disposed external to the FAIMS analyzer region, irradiating the target plate with light of a predetermined wavelength, the light of a predetermined wavelength selected to affect the sample material applied to the target plate so as to produce ions of the sample material; directing the ions of the sample material along an ion flow path between the target plate and FAIMS analyzer region, via the ion inlet orifice; and, directing a flow of a gas counter-current to the ion flow path and passing through the target plate.

The entire contents of U.S. Provisional Application No. 60/537,881 filed Jan. 22, 2004, are incorporated by reference herein.

BRIEF DESCRIPTION OF THE DRAWINGS

Exemplary embodiments of the invention will now be described in conjunction with the following drawings, in which similar reference numerals designate similar items:

FIG. 5a is a simplified longitudinal cross sectional view of a system according to another embodiment of the instant invention, including an atmospheric pressure MALDI ionization source, and a FAIMS;

FIG. 5b is a simplified top view of a target plate for use with the apparatus shown at FIG. 5a;

FIG. 6a is an expanded view of the ion inlet region of the system shown at FIG. 5a;

FIG. 6b is an expanded view of an optional arrangement of the ion inlet region of the system shown at FIG. 5a;

FIG. 6c is an expanded view of another optional arrangement of the ion inlet region of the system shown at FIG. 5a;

DESCRIPTION OF EMBODIMENTS OF THE INSTANT INVENTION

Exemplary embodiments of the invention will now be described in conjunction with the accompanying drawings. The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein.

Throughout the detailed description, reference is made primarily to atmospheric pressure MALDI, although it is to be understood that other atmospheric pressure ionization techniques, particularly laser based techniques such as atmospheric pressure laser desorption chemical ionization (AP/LD/CI), are readily interfaced to FAIMS using the general concepts presented herein. Furthermore, for the following discussions it is inconvenient to list all the possible versions of atmospheric pressure laser desorption chemical ionization (AP/LD/CI), atmospheric pressure matrix assisted laser desorption ionization (MALDI), and so on, that appear in the literature. Accordingly, the word MALDI is used as a representative example of one of many laser based ionization schemes that are appropriate for producing ions within the context of the embodiments of the instant invention. The laser optionally desorbs the molecules of interest from a surface, a matrix or a polymer support as some non-limiting examples, and the laser beam may or may not be involved in the ionization process. Optionally, hybrid schemes that include more than one process are used to produce ions. For example, ions are produced as a result of the sequential steps of laser desorption followed by ionization by means of a second laser for multi-photon excitation. In another example, molecules of a sample are volatilized from a surface by means of a laser and the vaporized molecules are ionized by gas-phase chemical ionization using a remotely produced reactant ion. These examples are presented merely to illustrate the diverse nature of ionization methods appropriate for the embodiments of the invention described below, and are not intended to limit the scope of possible laser-based ionization methods that can be used in conjunction with the instant invention. The instant invention addresses the problem of combining a laser beam and sample holder and presents a mechanism for desolvating and delivering ions into a FAIMS for ion separation.

Figure 1:
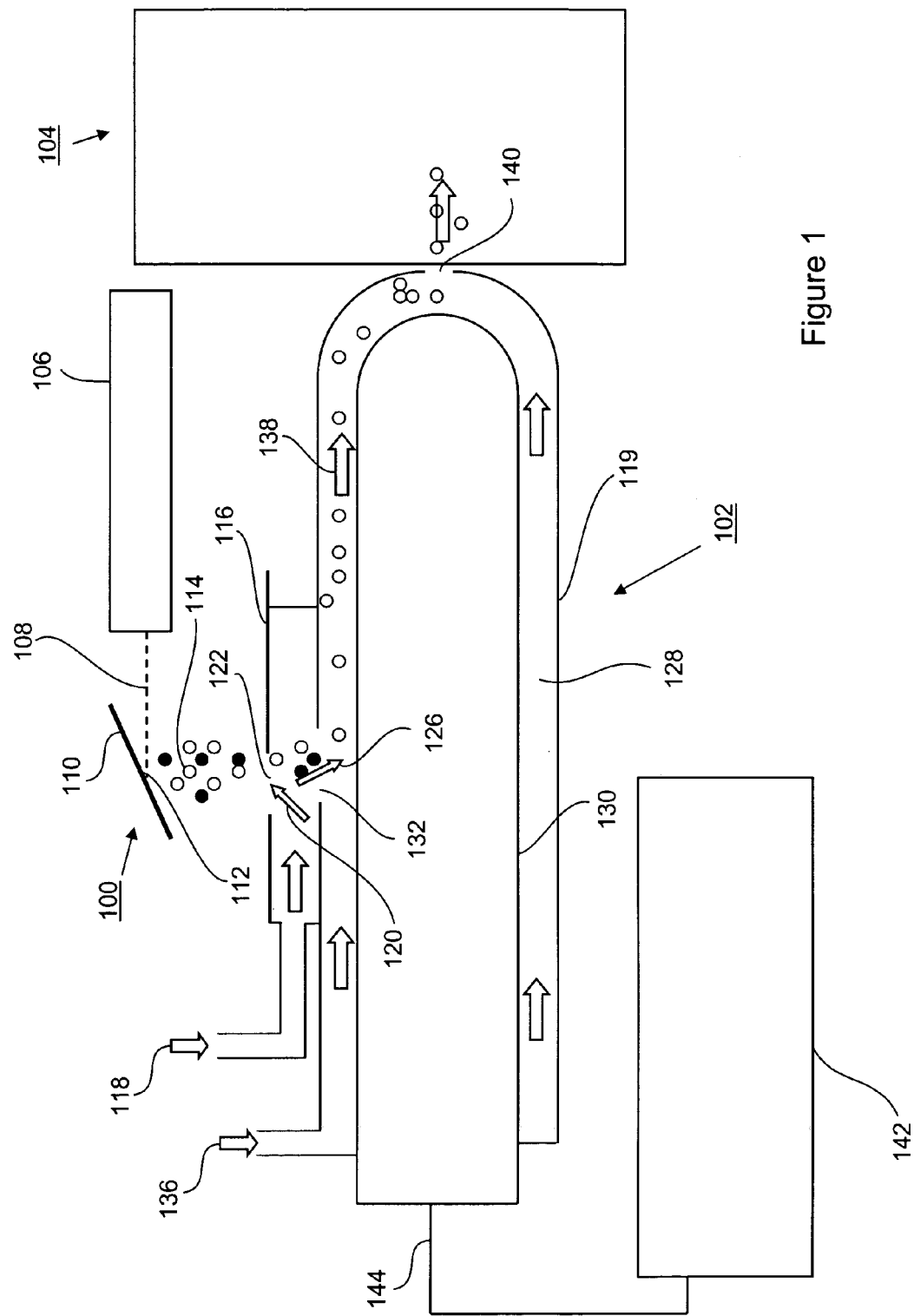
FIG. 1 is a simplified longitudinal cross sectional view of a system including an atmospheric pressure MALDI ionization source, a FAIMS, and a detection system.

Referring now to FIG. 1, shown is a simplified longitudinal cross sectional view of a system including an atmospheric pressure MALDI ion source 100, a FAIMS 102, and a detection system 104. The MALDI ion source 100 includes a laser source 106 that directs a laser beam 108 at a target plate 110 to which a sample spot 112 is applied. The laser beam 108 strikes the sample spot 112 and ionizes some of the compounds in the sample spot 112. The ion cloud 114 that is produced is directed towards a curtain plate 116 of FAIMS by application of voltages to the target plate 110 and to the curtain plate 116. A curtain gas flow 118 is provided between the curtain plate 116 and an outer electrode 119 of FAIMS. A portion 120 of the curtain gas flow 118 passes outwards through a curtain plate orifice 122, and an analyzer gas portion 126 flows into the analyzer region 128 between an inner FAIMS electrode 130 and the outer FAIMS electrode 119, via an ion inlet orifice 132. The flow of gas 120 that passes outwards through curtain plate orifice 122 serves to redirect away from the entrance to FAIMS the neutral molecules that are generated by the laser beam 108 striking the sample spot 112. Some of the ions 114 pass through the curtain plate orifice 122 and through the ion inlet orifice 132 into FAIMS 102. The ions 114 are propelled towards the ion inlet orifice 132 of FAIMS 102 by an electric field formed by a voltage difference between the curtain plate 116 and the outer electrode 119 of FAIMS. The gas flow 126 also assists in the transfer of ions into the FAIMS analyzer region 128.

After entering the analyzer region 128, the ions are carried by a carrier gas flow composed in part of the analyzer gas portion 126 and an optional additional gas flow 136. A high voltage asymmetric waveform and a direct current compensation voltage are applied to the inner electrode 130 by power supply 142 via an electrical coupling 144. Ion separation occurs within the analyzer region 128, between the ion inlet orifice 132 and the ion outlet orifice 140. The mixture 138 of ions and carrier gas travels to an ion outlet orifice 140 and into the detection system 104. The detection system 104 optionally includes further ion separation technologies including ion mobility, mass spectrometry, or FAIMS, and an ion detector such as for example one of an amperometric, photometric or electron multiplication detector.

The system shown at FIG. 1 is relatively simple, but in practice some problems are still encountered. In particular, the target plate 110 is not disposed parallel to the curtain plate 116, or more specifically parallel to the opening of the curtain plate orifice 122. Instead, the target plate 110 is positioned at an angle so as to support access by the laser beam 108. Because of this non-parallel arrangement, the electric fields between the target plate 110 and the curtain plate 116 are not ideal for directing the ions towards the curtain plate orifice 122. Preferably, the target plate 110 and the curtain plate 116 are parallel one relative to the other and arranged in close proximity so as to maximize the number of ions that enter FAIMS 102 via the curtain plate orifice 122.

Figure 2:
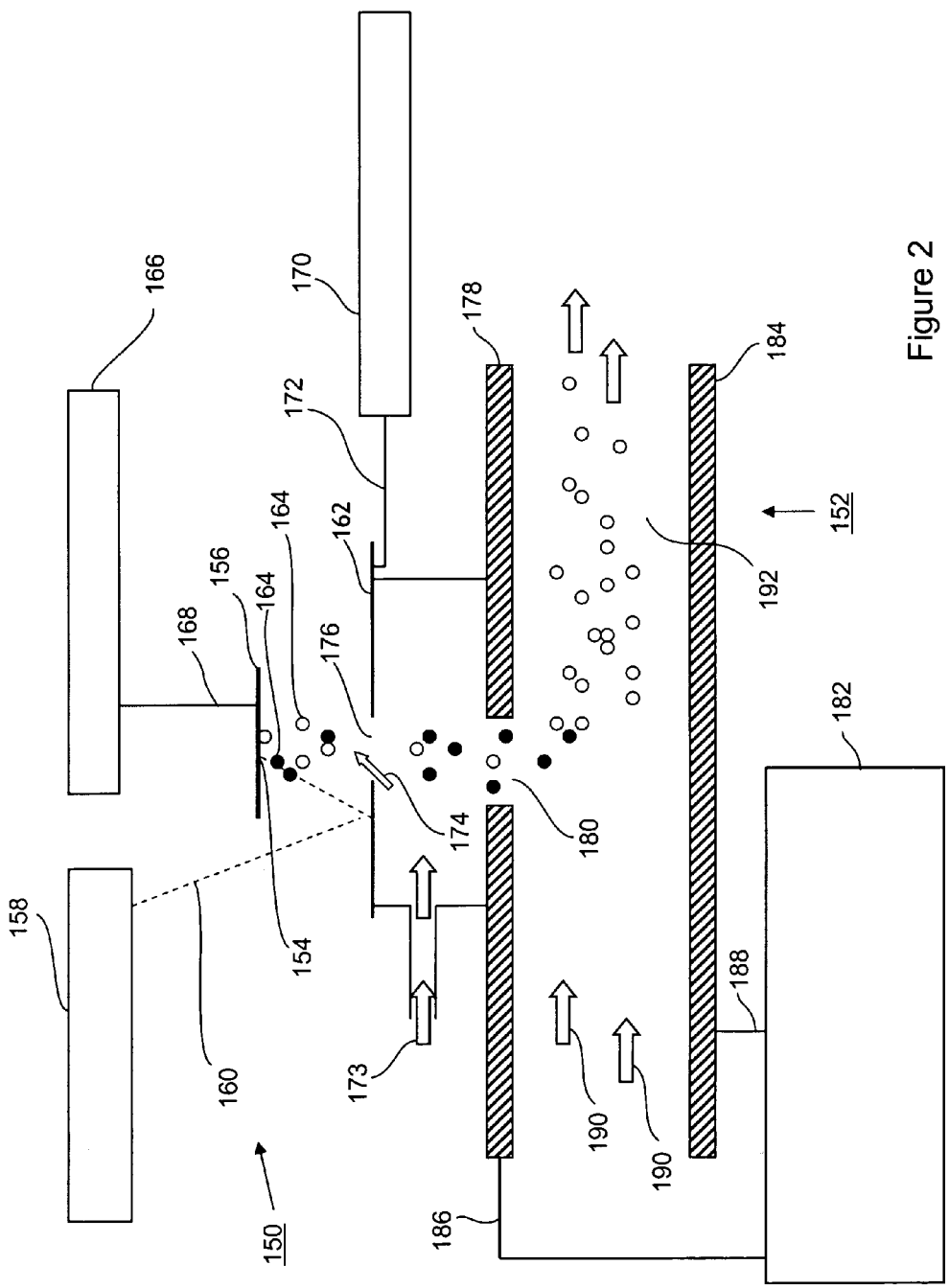
FIG. 2 is a simplified longitudinal cross sectional view of a system according to an embodiment of the instant invention, including an atmospheric pressure MALDI ionization source having a folded optical path and a FAIMS.

Referring now to FIG. 2, shown is a simplified longitudinal cross sectional view of a system according to an embodiment of the instant invention, including an atmospheric pressure MALDI ionization source 150 having a folded optical path, and a FAIMS 152. A sample spot 154 is applied to a target plate 156. Preferably, the target plate 156 is opaque and does not transmit light at a wavelength of laser light that is provided from a laser source 158. Optionally, the target plate 156 is electrically conductive. In the instant embodiment, the MALDI ionization source 150 has a folded optical path, such that the laser source 158 directs a laser beam 160 toward a polished surface of a curtain plate 162, which redirects the laser beam 160 toward the target plate 156 to which the sample spot 154 has been applied. The laser beam 160 strikes the sample spot 154 at an angle less than 90° and ionizes some of the compounds in the sample spot 154. The ion cloud 164 thus produced is directed towards the curtain plate 162 of FAIMS by application of voltages to the target plate 156 by power supply 166 via electrical coupling 168 and to the curtain plate 162 by power supply 170 via electrical coupling 172. Optionally, the power supply 166 and the power supply 170 are provided as a single electrical controller. During use, a flow of a curtain gas 173 is provided between the curtain plate 162 and, in this example, an upper FAIMS electrode 178. A portion 174 of the flow of a curtain gas 173 passes outwards through a port 176 in the curtain plate 162 and serves to redirect away from the entrance to FAIMS the neutral molecules that are generated by the laser beam 160 striking the sample spot 154, so as to prevent these neutral molecules from entering the space between the curtain plate 162 and the upper FAIMS electrode 178. Some of the ions are directed towards FAIMS 152 by electric fields that are generated by voltages applied to the target plate 156, the curtain plate 162 and the upper electrode 178 of FAIMS 152. Since the target plate 156 and curtain plate 162 are parallel to each other the ions are directed in an efficient manner from the target plate 156 towards the curtain plate 162. Some ions pass through the port 176 and are further directed towards FAIMS 152 and through an ion inlet orifice 180 by an electric field between the curtain plate 162 and the upper electrode 178 of FAIMS 152. The distance between the sample target plate 156 and the curtain plate 162 is established by optimization of the intensity of signals detected for the ions of interest. The ions that pass into FAIMS through the ion inlet orifice 180 are separated by application of a dispersion voltage (DV) and a compensation voltage (CV) by power supply 182 connected to the upper electrode 178 and a lower electrode 184 by electrical couplings 186 and 188, respectively. The voltages applied to the upper electrode 178 and the lower electrode 184 create electric fields between these electrodes that separate the ions while the ions are transported by a flow of carrier gas 190 along an analyzer region 192 between the upper electrode 178 and lower electrode 184. In FIG. 2 the upper electrode 178 and the lower electrode 184 are shown as parallel conductive flat plates, but are optionally micromachined (MEMS) parallel non-curved or curved surfaces, or further optionally, are non-conductive materials that are coated with a conductive layer as some non-limiting examples of FAIMS electrodes.

Figure 3:
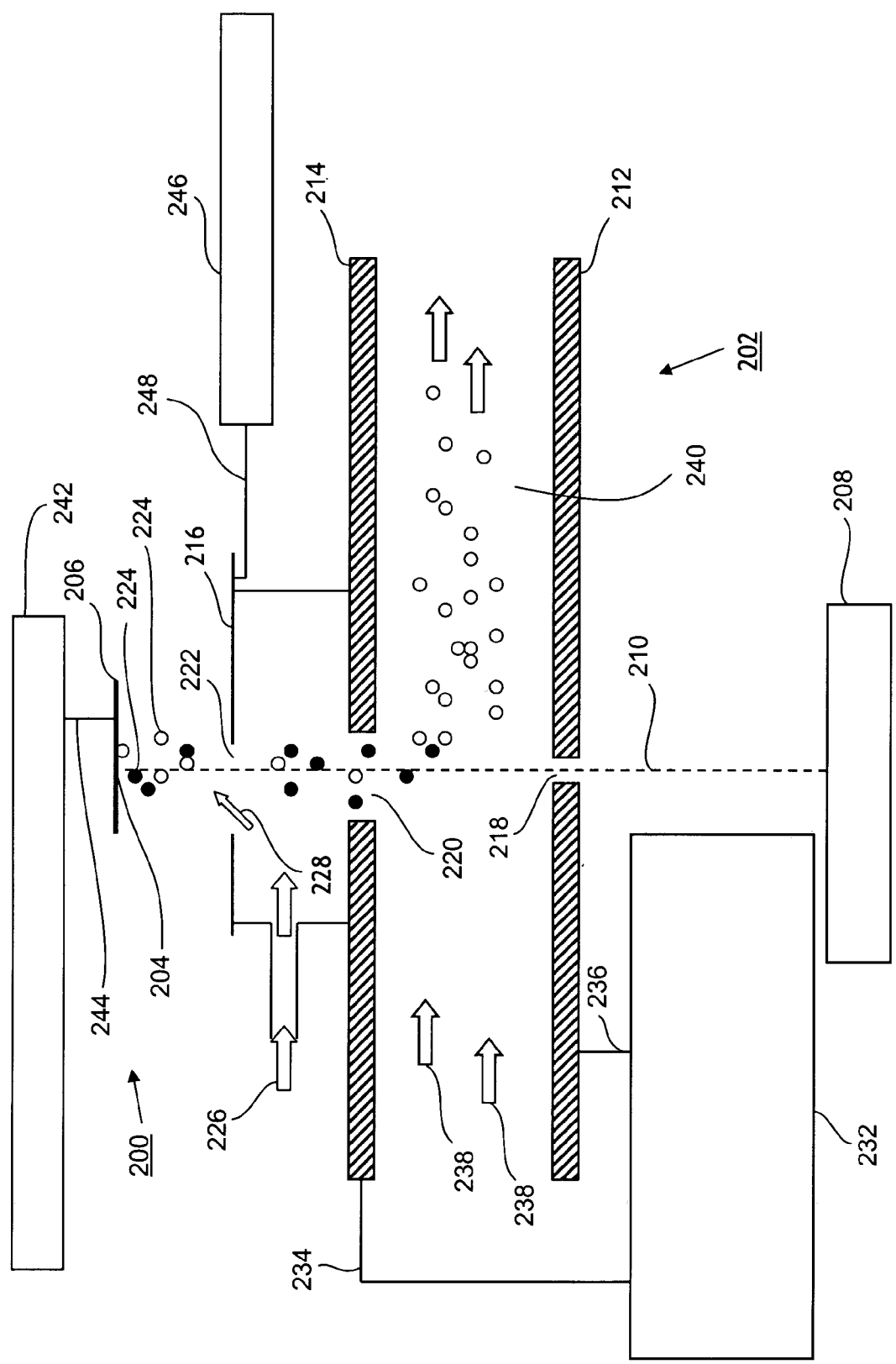
FIG. 3 is a simplified longitudinal cross sectional view of a system according to another embodiment of the instant invention, including an atmospheric pressure MALDI ionization source and a FAIMS.

Referring now to FIG. 3, shown is a simplified longitudinal cross sectional view of a system according to another embodiment of the instant invention, including an atmospheric pressure MALDI ion source 200, and a FAIMS 202. A sample spot 204 is applied to a target plate 206. Preferably, the target plate 206 is opaque and does not transmit light at a wavelength of laser light provided from a laser source 208. Optionally, the target plate 206 is electrically conductive. A laser beam 210 is projected from the laser light source 208, through electrodes 212 and 214 of FAIMS 202, and out through a curtain plate 216 to strike the sample spot 204 and ionizes some of the compounds in the sample spot 204. In particular, the laser beam 210 passes through a laser orifice 218 defined within the lower electrode 212 of FAIMS 202, through an ion inlet orifice 220 defined within the upper electrode 214 of FAIMS 202, and through a port 222 of curtain plate 216. By passing the laser beam 210 through port 222 of curtain plate 216, the laser beam 210 strikes the sample spot 204 at an angle close to perpendicular to the target plate 206.

Referring still to FIG. 3, the laser beam 210 strikes the sample spot 204 and an ion cloud 224 thus produced is directed towards the curtain plate 216 of FAIMS 202 by application of voltages to the target plate 206 by power supply 242 via electric coupling 244 and to the curtain plate 216 by power supply 246 via electrical coupling 248. A curtain gas flow 226 is provided in the space between the curtain plate 216 and the upper electrode 214 of FAIMS 202. A portion 228 of the curtain gas flow 226 passes outwards through port 222 and serves to redirect away from the entrance to FAIMS 202 the neutral molecules that are generated by the laser beam 210 striking the sample spot 204, and prevents these neutral molecules from entering the space between the curtain plate 216 and the upper FAIMS electrode 214. At the same time, the ions 224 are directed towards FAIMS 202 by electric fields generated by voltages applied to the target plate 206, the curtain plate 216 and the upper electrode 214 of FAIMS. Since the target plate 206 and curtain plate 216 are parallel to each other the ions are directed in an efficient manner from the target plate 206 towards the curtain plate 216. The target plate 206 and curtain plate 216 are sufficiently close together to maximize the likelihood of ions produced from the sample spot 204 entering the port 222 of the curtain plate 216. However, the space between the target plate 206 and the curtain plate 216 is sufficiently wide that the velocity of gas flow 228 is low, such that gas flow 228 does not drive ions away from the region in front of the port 222. The ions pass through the port 222 and are further directed towards ion inlet orifice 220 in the upper electrode 214 of FAIMS 202 by the electric field between the curtain plate 216 and the upper electrode 214 of FAIMS. The distance between the sample target plate 206 and the curtain plate 216 is established by optimization of the intensity of signals detected for the ions of interest.

The ions in FAIMS are separated by application of DV and CV by power supply 232 connected to the upper electrode 214 and the lower electrode 212 by electrical couplings 234 and 236, respectively. The voltages applied to the upper electrode 214 and the lower electrode 212 create electric fields between these electrodes that separate the ions while the ions are transported by a flow of carrier gas 238 along an analyzer region 240 between the upper electrode 214 and lower electrode 212. In FIG. 3 the upper electrode 214 and the lower electrode 212 are shown as parallel conductive flat plates, but are optionally micromachined (MEMS) parallel non-curved or curved surfaces, or further optionally are non-conductive materials that are coated with a conductive layer as some non-limiting examples of FAIMS electrodes. Note also that it is necessary to prevent contamination from entering the gas flow in FAIMS through the laser orifice 218. This can optionally be accomplished by providing a window at laser orifice 218 through which the laser is directed, or a flow of gas outwards through laser orifice 218 to carry away potential contaminants.

Figure 4:
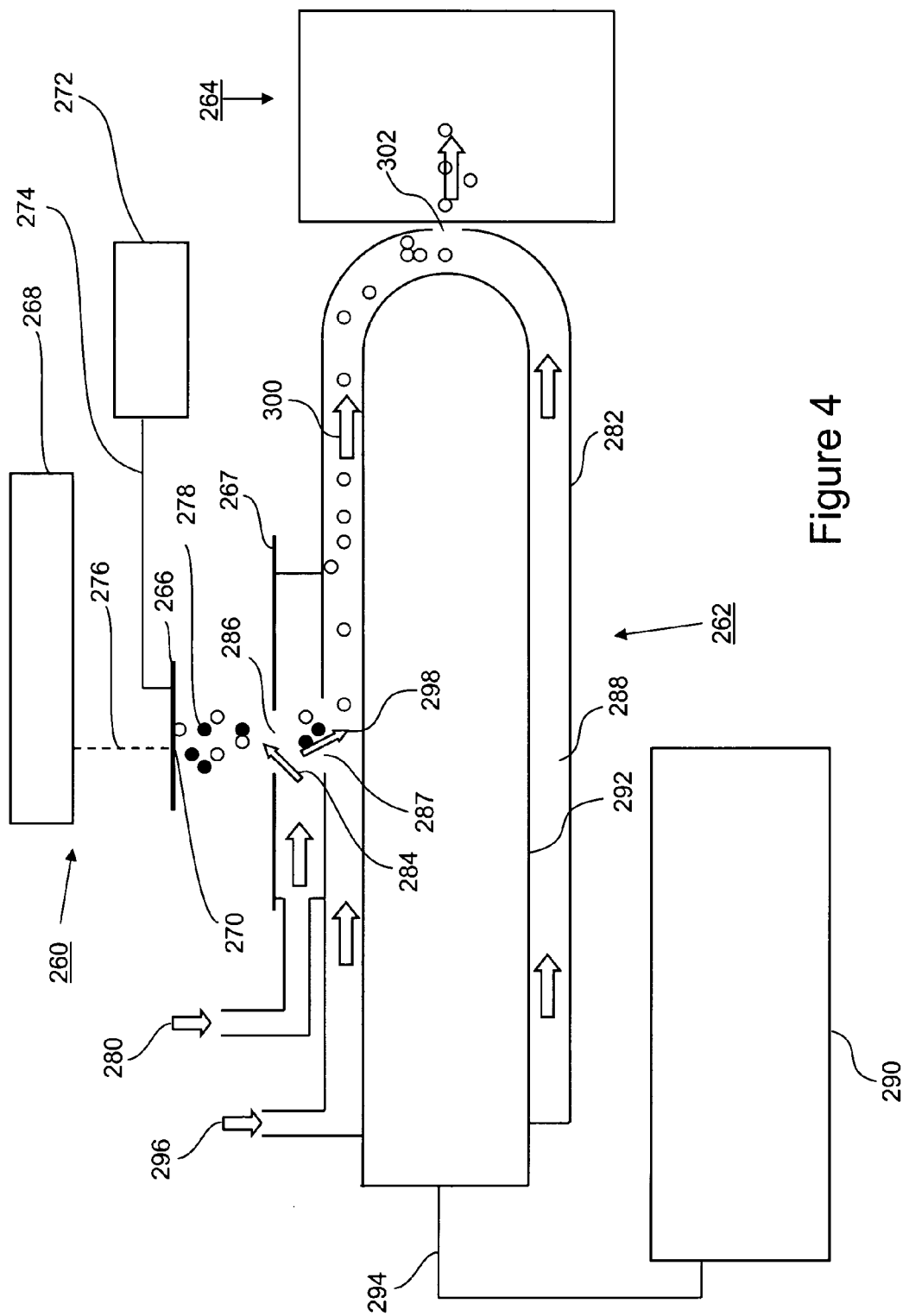
FIG. 4 is a simplified longitudinal cross sectional view of a system according to another embodiment of the instant invention, including an atmospheric pressure MALDI ionization source, a FAIMS, and a detection system.

Referring now to FIG. 4, shown is a simplified longitudinal cross sectional view of a system according to an embodiment of the instant invention, including an atmospheric pressure MALDI ionization source 260, a FAIMS 262, and a detection system 264. The apparatus shown at FIG. 4 includes a target plate 266 that is disposed parallel to and in close proximity to a curtain plate 267 of FAIMS 262. Furthermore, the target plate 266 is at least partially transparent to light of a wavelength that is provided by a laser source 268. Optionally, the target plate is partly transparent to the laser light. During use, a sample spot 270 is applied to the target plate 266. Preferably, the target plate 266 is also at least partly conductive so as to maintain the voltages that are applied to the target plate 266 by power supply 272 via electrical coupling 274, and to minimize electric charging of the target plate 266 caused by ionization of the sample spot 270. A laser beam 276 is directed from the laser source 268 to impinge upon or strike a back surface of the target plate 266. Some of the laser light is transmitted through the target plate 266 and ionizes some of the compounds in the sample spot 270. The ion cloud 278 that is produced is directed towards the curtain plate 267 of FAIMS by application of voltages to the target plate 266 and to the curtain plate 267. A curtain gas flow 280 is provided within the space between the curtain plate 267 and an outer electrode 282 of FAIMS. A portion 284 of the curtain gas flow 280 passes outwardly through a curtain plate orifice 286 and serves to redirect away from the entrance to FAIMS the neutral molecules that are generated by the laser beam 276 striking the sample spot 270. The ions 278 are directed towards FAIMS by electric fields generated by voltages applied to the target plate 266, to the curtain plate 267 and to the outer electrode 282 of FAIMS. Since the target plate 266 and curtain plate 267 are disposed parallel to each other, the ions are directed in an efficient manner from the target plate 266 towards the curtain plate 267. Some ions pass through the curtain plate orifice 286 and are further directed towards FAIMS and through an ion inlet orifice 287 into a FAIMS analyzer region 288 by the electric field between the curtain plate 268 and the outer electrode 282 of FAIMS. If a portion 298 of the curtain gas flows into the analyzer region 288 between an inner electrode 292 and the outer electrode 282, this gas flow 298 (the analyzer gas portion) also assists in the transfer of ions into FAIMS. The ions are carried through the FAIMS analyzer region 288 by a carrier gas flow composed in part of the analyzer gas portion 298 and an optional additional gas flow 296. The ions in FAIMS are separated by application of DV and CV by power supply 290 connected to the inner electrode 292 of FAIMS via an electrical coupling 294. The voltages applied to the inner electrode 292 create electric fields between the inner electrode 292 and the outer electrode 282 that separate the ions while the ions are transported along the analyzer region 288. The mixture 300 of ions and carrier gas travels to an ion outlet orifice 302 and into the detection system 264. The detection system 264 optionally includes further ion separation technologies including ion mobility, mass spectrometry, or FAIMS, and an ion detector such as for example one of an amperometric, photometric or electron multiplication detector. The distance between the sample target plate 266 and the curtain plate 268 is established by optimization of the intensity of signals detected for the ions of interest.

In FIGS. 2 through 4, the ions produced at the target plate must travel towards the curtain plate and pass through a curtain plate orifice before approaching the ion inlet orifice. Furthermore, the greater the distance the ions must travel between the target plate and the ion inlet orifice into FAIMS, the lower the ion transmission efficiency. For instance, ions are lost to the surface of the curtain plate and also as a result of recombination of positively charged ions and negatively charged ions, both of which are produced simultaneously by a MALDI ionization source. Accordingly, it is preferable to minimize the distance between the target plate of the MALDI ionization source and the ion inlet orifice into the FAIMS analyzer region. It is further preferable to eliminate many of the surfaces that may cause ion loss along the ion path, in order to maximize the percentage of the ions of interest that are introduced into the analyzer region. It is also beneficial to minimize the number of neutral molecules, and non-ionized compounds and droplets, entering the FAIMS analyzer region.

Referring now to FIG. 5a, shown is a simplified longitudinal cross sectional view of a system according to an embodiment of the instant invention, including an atmospheric pressure MALDI ionization source 310, and a FAIMS 312. The system shown at FIG. 5a operates with a modified curtain gas approach for preventing neutrals from entering FAIMS 312. A sample spot 314 is applied to a target plate 316, which is mounted to a FAIMS upper electrode 320 in a gas-tight fashion (meaning that gas cannot readily escape between the target plate 316 and FAIMS upper electrode 320).

Referring now to FIG. 5a and FIG. 5b, the target plate 316 is fabricated from a material with some electrical conductivity. The target plate 316 is fabricated from a material that is at least partly and/or partially transparent to laser light of a wavelength that is provided by a laser source 318. Furthermore, the target plate 316 is at least partly porous or permeable to a flow of a carrier gas 324, such that a portion 326 of the carrier gas 324 is transmitted through the target plate 316 and therefore carries away neutral molecules generated when a laser beam 328 originating at laser source 318 strikes the sample spot 314. For instance, the target plate 316 is fabricated from a fine metallic mesh or a fine metal screen that has the desired properties of transparency to the laser beam, electrical conductivity and porosity for passage of the flow 326 of a portion of a carrier gas 324 out through the ion inlet orifice 322. Although the target plate 316 is shown as being circular in shape in the instant embodiment, optionally the target plate is any other suitable shape such as for example square or rectangular. In the case of a curved upper FAIMS electrode 320 (or optionally a not illustrated cylindrically shaped FAIMS outer electrode) the target plate 316 is optionally curved also.

During use, the laser beam 328 is directed to strike the back surface of the target plate 316, while the sample spot is located at the front surface of the target plate 316 facing into an analyzer region 330 of FAIMS between the FAIMS upper electrode 320 and a FAIMS lower electrode 334. A portion of the laser light is transmitted through the target plate 316 to the sample spot 314 and ionizes some of the compounds in the sample spot 314. Ions 332 that are produced by the laser beam 328 striking the sample sport 314 are directed into the FAIMS analyzer region 330 by electric fields generated by voltages applied to the target plate 316, and to the upper electrode 320 of FAIMS. The ions are separated within the FAIMS analyzer region 330 by application of DV and CV using power supply 336, which is connected to the FAIMS upper electrode 320 and the lower electrode 334 via electrical couplings 338 and 340, respectively. The voltage differences applied between the upper electrode 320 and the lower electrode 334 create electric fields between these electrodes. The ions are separated under the influence of these electric fields as they are being transported by a flow of he carrier gas 324 (minus the gas flow 326 that passes outward through the target plate 316) along the analyzer region 330 between the FAIMS upper electrode 320 and the FAIMS lower electrode 334.

Advantageously, the ions 332 pass almost immediately into the FAIMS analyzer region 330 via ion inlet orifice 322 without traversing a separate curtain gas region that is external to the FAIMS analyzer region 330. Once inside the FAIMS analyzer region 330, those ions that do not posses stable trajectories under the influence of the applied CV and DV are lost rapidly to an electrode surface. Accordingly, the probability of an ion of interest recombining with another ion of opposite polarity is reduced. Furthermore, the neutral molecules generated when the laser beam 328 strikes the sample spot 314 are prevented from entering the FAIMS analyzer region 330 by the flow of gas 326 outwards through the target plate 316.

FIG. 5*a*, the FAIMS upper electrode 320 and the FAIMS lower electrode 334 are shown as planar conductive electrodes. Optionally, electrodes having other FAIMS electrode geometries are used, such as for instance micromachined (MEMS) parallel non-curved or curved surfaces. Further optionally, the electrodes are fabricated from non-conductive materials and are coated with a conductive outer layer.

Figure 6A:
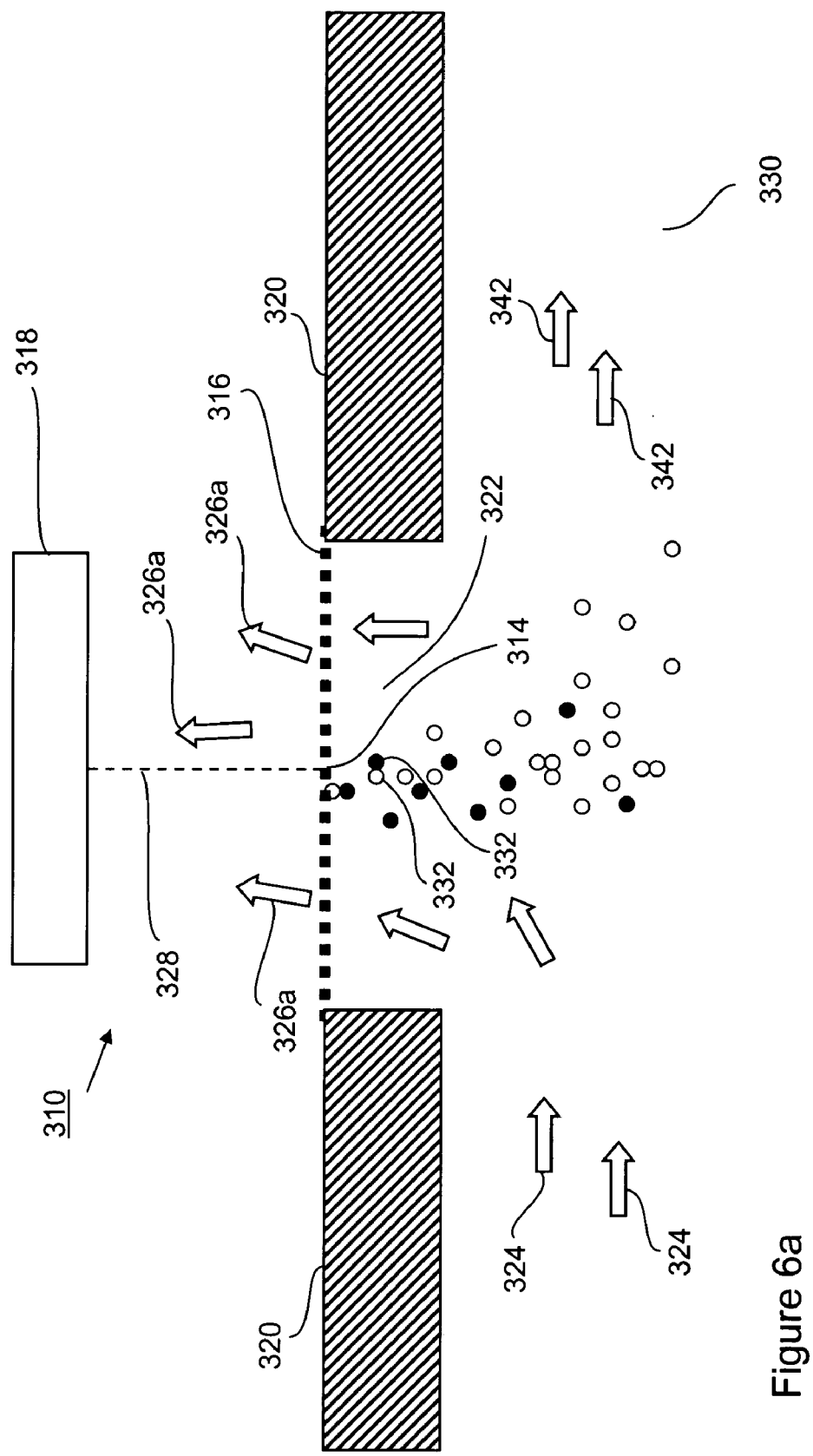

Referring now to FIG. 6*a*, shown is an expanded view of the ion inlet region of the MALDI-FAIMS system that is shown in FIG. 5*a*. Elements labeled with the same numerals have the same function as those illustrated in FIG. 5*a*. The target plate 316 is mounted in a gas-tight manner to the FAIMS upper electrode 320, and is in electrical communication with the FAIMS upper electrode 320. Optionally, a not illustrated insulating spacer is disposed between the target plate 316 and the upper electrode 320, to permit a voltage to be applied to the target plate 316 that is different from a voltage that is applied to the upper electrode 320, such as for the purpose of aiding in directing ions generated by the laser beam 328 towards the FAIMS analyzer region 330. In the embodiment shown at FIG. 6*a*, the target plate 316 is at least partly porous and supports a flow of gas 326*a* therethrough. The sample spot 314 is applied to the front surface of the target plate 316, preferably with the target plate moved away from the FAIMS (during a sample application step, not shown here). Optionally, the sample is sprayed onto the target plate 316, at a sample preparation station that is designed for this purpose. The laser beam 328 generated by laser source 318 is directed to the back side of the target plate 316. Accordingly, the target plate 316 is fabricated from a material that is at least partially transparent to light of a wavelength provided by laser source 318. Optionally, the target plate 316 is also at least partly electrically conductive. Further optionally, the target plate 316 is fabricated from a metallic mesh material or a fine metal screen, and the sample therefore readily distributes by capillary action to both sides of the material. Further optionally, the target plate material is a partially transparent material other than a metallic mesh, but with some electrical conductivity and with holes or perforations that give the target plate the required porosity for supporting the outward flow of gas 326*a*. Optionally, the sample spot 314 is applied to a portion of the target plate 316 without holes, and the gas flow 326*a* exits through holes in the immediate vicinity of the sample spot 314.

Still referring to FIG. 6*a*, some of the carrier gas 324 that is supplied to the analyzer region 330 between the FAIMS upper electrode 320 and the not illustrated FAIMS lower electrode flows out through the ion inlet orifice 322 in the FAIMS upper electrode 320, and flows out though the target plate 316. This outward gas flow 326*a* assists in preventing neutral molecules that evaporate from the sample spot 314, and neutral molecules that are evolved as a plume when the laser hits the sample spot 314, from passing into the FAIMS analyzer region 330. The total carrier flow 324 provided into the analyzer region 330 is therefore divided into two streams, one stream 326*a* exiting through the target plate 316 and a second stream 342 that transports the ions through the FAIMS analyzer region 330 to a not illustrated ion outlet.

Figure 6B:
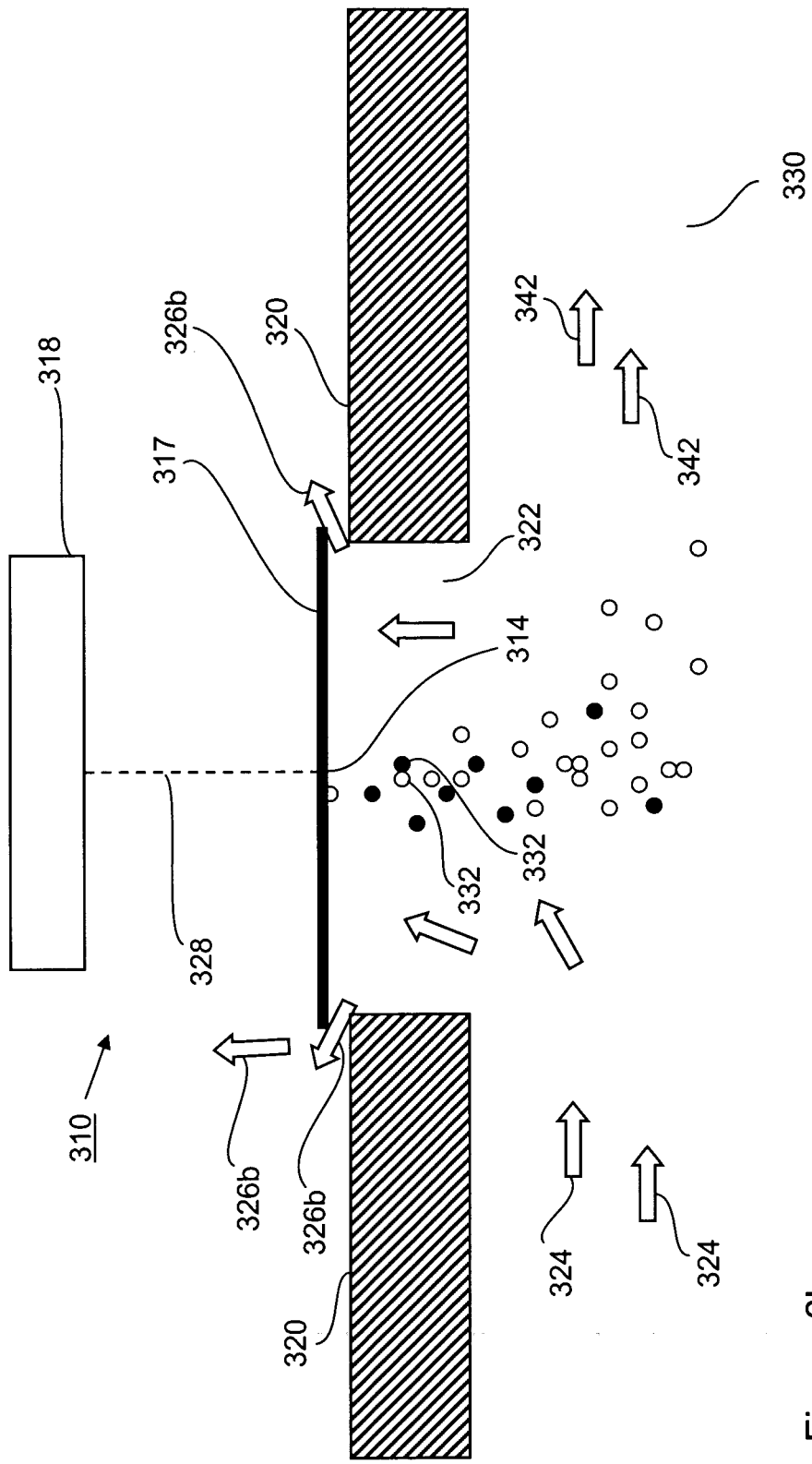

Referring now to FIG. 6*b*, shown is an expanded view of an optional arrangement of the ion inlet region of the system shown at FIG. 5*a*. Elements labeled with the same numerals have the same function as those illustrated in FIG. 5*a*. The target plate 317 is mounted slightly spaced apart from the FAIMS upper electrode 320, such that a gap is provided between the target plate 317 and the upper electrode 320, as is shown in FIG. 6*b*. In the embodiment shown at FIG. 6*b*, the target plate 317 is not porous and does not support a flow of gas therethrough. The sample spot 314 is applied to the front surface of the target plate 317, preferably with the target plate moved away from the FAIMS (during a sample application step, not shown here). Optionally, the sample is sprayed onto the target plate 317, at a sample preparation station that is designed for this purpose. The laser beam 328 generated by laser source 318 is directed to the back side of a target plate 317. Accordingly, the target plate is fabricated from a material is at least partially transparent to light of a wavelength provided by laser source 318. Optionally, the target plate is also at least partly electrically conductive.

Still referring to FIG. 6*b*, some of the carrier gas 324 that is supplied to the analyzer region 330 between the FAIMS upper electrode 320 and the not illustrated FAIMS lower electrode flows out through the ion inlet orifice 322 in the FAIMS upper electrode 320, and flows out though the space between the target plate 317 and the FAIMS upper electrode 320. This outward gas flow 326*b* assists in preventing neutral molecules that evaporate from the sample spot 314, and neutral molecules that are evolved as a plume when the laser hits the sample spot 314, from passing into the FAIMS analyzer region 330. The total carrier flow 324 provided into the analyzer region 330 is therefore divided into two streams, one stream 326*b* exiting between the target plate 317 and the FAIMS upper electrode 320, and a second stream 342 that transports the ions through the FAIMS analyzer region 330 to a not illustrated ion outlet. The target plate 317 and FAIMS upper electrode 320 are sufficiently close together to maximize the likelihood of ions produced from the sample spot 314 entering the ion inlet orifice 322. However, the space between the target plate 317 and the FAIMS upper electrode 320 is sufficiently wide that the velocity of gas flow 326*b* is low, such that gas flow 326*b* does not drive ions away from the region in front of the ion inlet orifice 322.

Figure 6C:
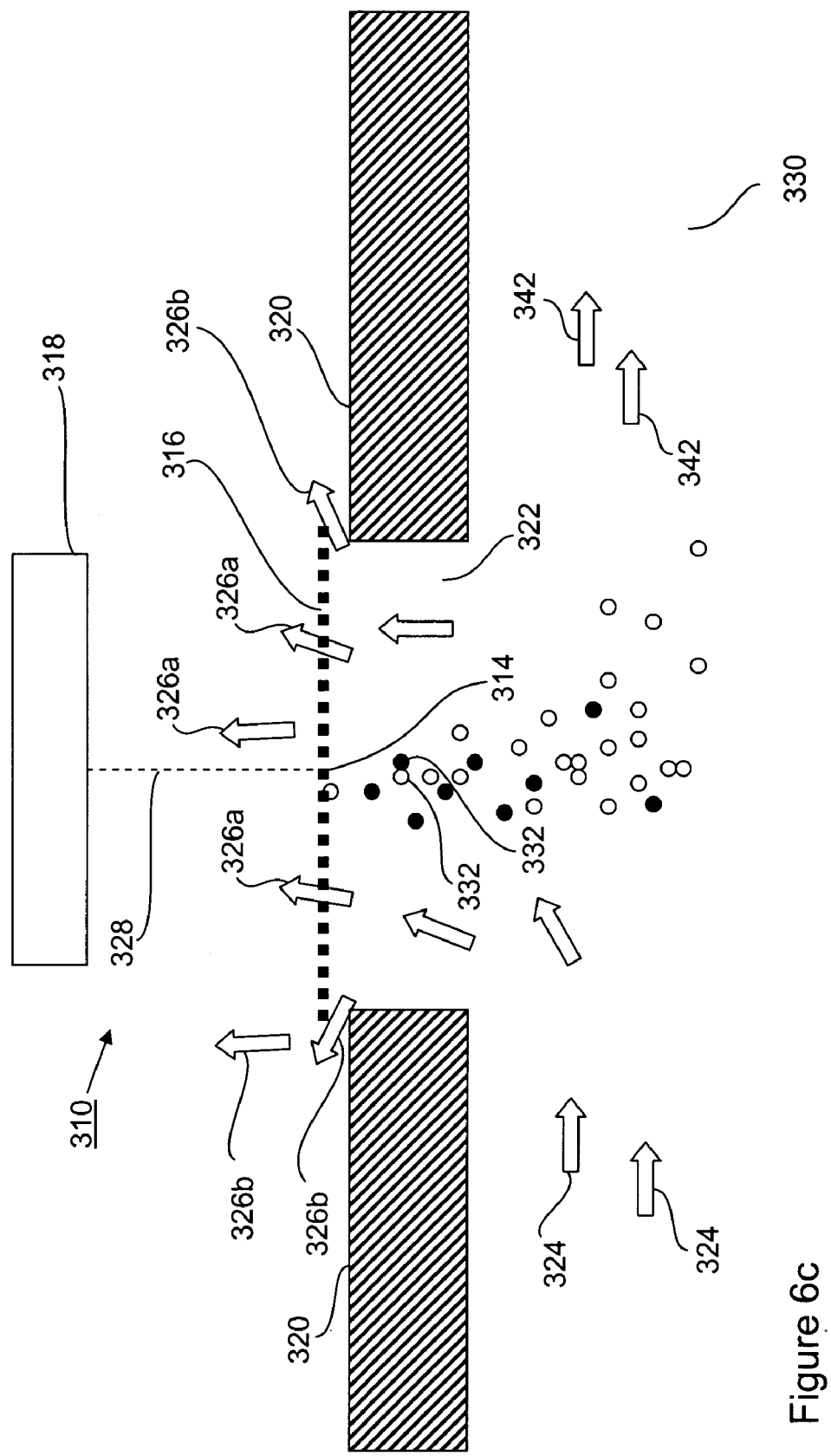

Referring now to FIG. 6*c*, shown is an expanded view of another optional arrangement of the ion inlet region of the system shown at FIG. 5*a*. Elements labeled with the same numerals have the same function as those illustrated in FIG. 5*a*. The target plate 316 is mounted slightly spaced apart from the FAIMS upper electrode 320, such that a gap is provided between the target plate 316 and the upper electrode 320, as is shown in FIG. 6*c*. In the embodiment shown at FIG. 6*c*, the target plate 316 is also at least partly porous and supports a flow of gas 326*a* therethrough. The sample spot 314 is applied to the front surface of the target plate 316, preferably with the target plate moved away from the FAIMS (during a sample application step, not shown here). Optionally, the sample is sprayed onto the target plate 316, at a sample preparation station that is designed for this purpose. The laser beam 328 generated by laser source 318 is directed to the back side of the target plate 316. Accordingly, the target plate 316 is fabricated from a material is at least partially transparent to light of a wavelength provided by laser source 318. Optionally, the target plate is also at least partly electrically conductive. Further optionally, the target plate 316 is fabricated from a metallic mesh material or a fine metal screen, and the sample therefore readily distributes by capillary action to both sides of the target plate 316. Further optionally, the target plate material is a partially transparent material other than a metallic mesh, but with some electrical conductivity and with holes or perforations that give the target plate the required porosity for supporting the outward flow of gas 326a. Optionally, the sample spot 314 is applied to a portion of the target plate 316 without holes, and the gas flow 326a exits through holes in the immediate vicinity of the sample spot 314.

Still referring to FIG. 6c, some of the carrier gas 324 that is supplied to the analyzer region 330 between the FAIMS upper electrode 320 and the not illustrated FAIMS lower electrode flows out through the ion inlet orifice 322 in the FAIMS upper electrode 320, and flows out though the target plate 316 as gas flow 326a. In addition, some of the carrier gas 324 that is supplied to the analyzer region 330 between the FAIMS upper electrode 320 and the not illustrated FAIMS lower electrode flows out through the ion inlet orifice 322 in the FAIMS upper electrode 320, and flows out though the space between the target plate 317 and the FAIMS upper electrode 320 as gas flow 326b. The target plate 316 and FAIMS upper electrode 320 are sufficiently close together to maximize the likelihood of ions produced from the sample spot 314 entering the ion inlet orifice 322. However, the space between the target plate 316 and the FAIMS upper electrode 320 is sufficiently wide that the velocity of gas flow 326b is low, such that gas flow 326b does not drive ions away from the region in front of ion inlet orifice 322. The outward gas flows 326a and 326b assist in preventing neutral molecules that evaporate from the sample spot 314, and neutral molecules that are evolved as a plume when the laser hits the sample spot 314, from passing into the FAIMS analyzer region 330. The total carrier flow 324 provided into the analyzer region 330 is therefore divided into two streams, one stream 326a and 326b exiting through the ion inlet orifice 322 and a second stream 342 that transports the ions through the FAIMS analyzer region 330 to a not illustrated ion outlet.

Figure 7:
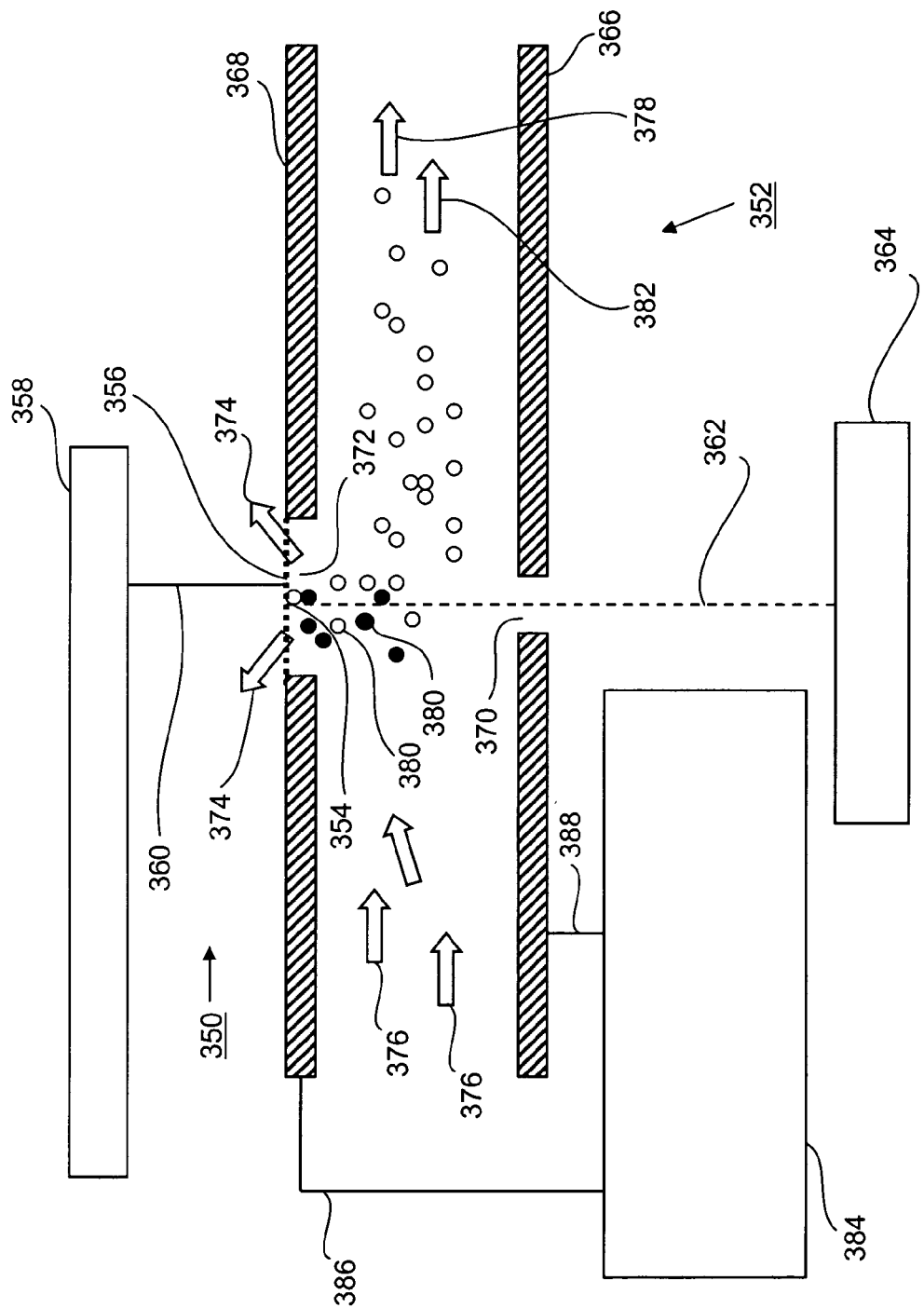
FIG. 7 is a simplified longitudinal cross sectional view of a system according to another embodiment of the instant invention, including an atmospheric pressure MALDI ionization source, and a FAIMS.

Referring now to FIG. 7, shown is a simplified longitudinal cross sectional view of a system according to another embodiment of the instant invention, including an atmospheric pressure MALDI ionization source 350, and a FAIMS 352. During use, a sample spot 354 is applied to a target plate 356. A power supply 358 is used to apply a voltage to the target plate 356 through an electrical coupling 360. During use, a laser beam 362 is projected from a laser light source 364, through electrodes 366 and 368 of FAIMS 352, to strike the sample spot 354 and ionize some of the compounds in the sample spot 354. In particular, the laser beam 362 passes through a laser orifice 370 defined within the lower electrode 366 of FAIMS, and through an ion inlet orifice 372 defined within the upper electrode 368 of FAIMS. By passing the laser beam 362 through ion inlet orifice 372 of upper electrode 368, the laser beam 362 strikes the sample spot 354 at an angle close to perpendicular to the target plate 356. The neutral molecules that are generated when the laser beam 362 strikes the sample spot 354 are prevented from entering FAIMS by an outward flow of gas 374 that originates as part of an excess flow of carrier gas 376. The flow of carrier gas 376 is the sum of the outward flow of gas 374 and the gas 378 (arrows shown) that leaves FAIMS through the not illustrated ion and gas exit ports. This outward gas flow 374 assists in preventing neutral molecules that evaporate from the sample spot 354, and neutral molecules that are evolved as a plume when the laser hits the sample spot 354, from passing into the FAIMS analyzer region 382. The target plate 356 is at least partly porous or permeable to the flow of carrier gas 376, so as to support the outward flow of gas 374 therethrough. For instance, the target plate 356 is fabricated from a fine metallic mesh or a fine metal screen that has the desired properties of electrical conductivity and porosity for passage of the flow 374 of a portion of a carrier gas 376 out through the ion inlet orifice 372.

The ions that pass into FAIMS are separated by application of DV and CV voltages by power supply 384 connected to the upper electrode 368 and the lower electrode 366 by electrical couplings 386 and 388, respectively. The differences in the voltages applied to the upper electrode 368 and the lower electrode 366 create electric fields between these electrodes that separate the ions while the ions are transported from the ion inlet 372 to a not illustrated ion outlet by the flow of carrier gas 378 (flow of gas 376 less the gas portion 374 that exits through ion inlet orifice 372) along the analyzer region 382 between the upper electrode 368 and lower electrode 366.

Optionally, a not illustrated insulating spacer is disposed between the target plate 356 and the upper electrode 368, to permit a voltage to be applied to the target plate 356 that is different from a voltage that is applied to the upper electrode 368, for the purpose of aiding in directing the ions of interest generated by the laser beam 362 towards the FAIMS analyzer region 382. Recall that laser ionization produces both positive and negative ions and that these ions may recombine. An electric field between the target plate 356 and the upper electrode 368 is one way of minimizing the likelihood of recombination. Further optionally, the target plate material is a partially transparent material other than a metallic mesh, but with some electrical conductivity and with holes or perforations that give the target plate the required porosity for supporting the outward flow of gas 374. Optionally, the sample spot 354 is applied to a portion of the target plate 356 without holes, and the gas flow 374 exits through holes in the immediate vicinity of the sample spot 354. Note also that it is necessary to prevent contamination from entering the gas flow in FAIMS through the laser orifice 370. This is achieved optionally by providing a window across the laser orifice 370 through which the laser is directed, or a flow of gas outwards through laser orifice 370 to carry away potential contaminants.

In FIG. 7 the upper electrode 368 and the lower electrode 366 are shown as parallel conductive plates, but optionally they are micromachined (MEMS) parallel non-curved or curved surfaces. Further optionally, the electrodes are made of non-conductive materials that are coated with a conductive layer. Many types of FAIMS geometry may optionally be used, including domed inner electrodes, side-to-side configurations, parallel plates, and spherical geometry, as some non-limiting examples.

Figure 8:
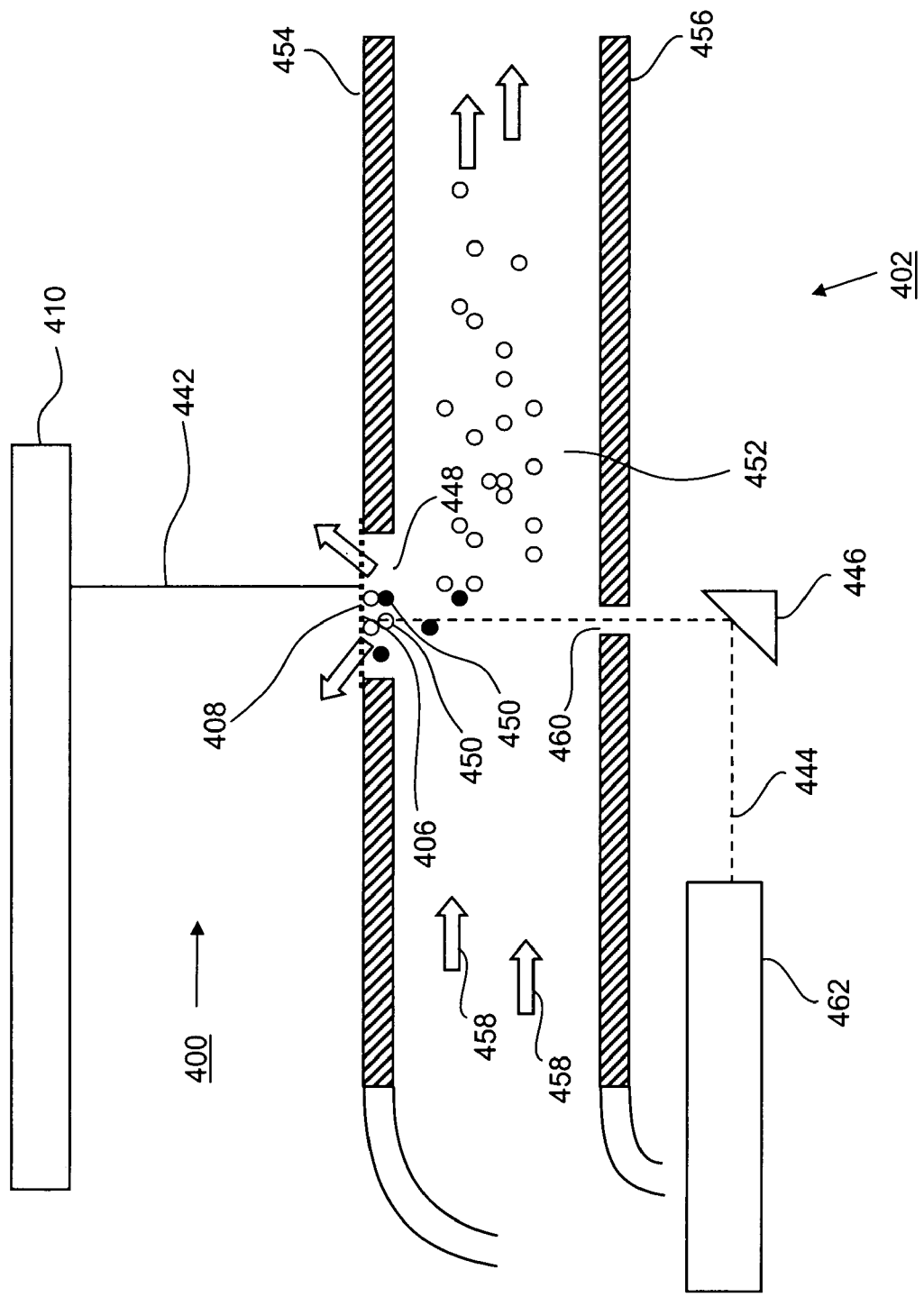
FIG. 8 is a simplified longitudinal cross sectional view of a system according to another embodiment of the instant invention, including an atmospheric pressure MALDI ionization source, and a FAIMS.

Referring now to FIG. 8, shown is a simplified longitudinal cross sectional view of a system according to another embodiment of the instant invention, including an atmospheric pressure MALDI ion source 400, and a FAIMS 402. A sample spot 406 is applied to a target plate 408. A power supply 410 is used to apply a voltage to the target plate 408 via an electrical coupling 442. A laser beam 444 is directed through the FAIMS electrodes via a reflective surface 446 to strike the sample spot 406 and ionizes some of the compounds in the sample spot 406. In this embodiment the laser beam strikes the sample spot 406 at an angle close to perpendicular to the target plate 408. In addition the target plate 408 and an ion inlet orifice 448 of FAIMS are in gas-tight connection.

Elimination of the curtain plate assembly that was shown in previous figures is beneficial for maximization of the ion transmission from MALDI to FAIMS. Optionally, the neutral molecules generated when the laser beam 444 strikes the sample spot 406 are allowed to enter FAIMS if it is determined that the presence of these neutral molecules is tolerable, or in some cases beneficial. It should be noted that small quantities of neutral molecules, including carbon dioxide, are in some cases beneficial due to formation of labile complexes that are created and dissociated during the cycles of the asymmetric waveform.

Still referring to FIG. 8, the laser beam 444 strikes the sample spot 406 and an ion cloud 450 thus produced is directed towards the analyzer region 452 between an outer electrode 454 and an inner electrode 456. The ions in FAIMS are separated by application of DV and CV voltages by a not illustrated power supply connected to the outer electrode 454 and the inner electrode 456 by not illustrated electrical couplings. The voltages applied to the outer electrode 454 and the inner electrode 456 create electric fields between these electrodes that separate the ions while the ions are transported by a flow of carrier gas 458 along the analyzer region 452 between the outer electrode 454 and inner electrode 456. In this diagram the outer electrode 454 and the inner electrode 456 are shown as coaxial cylindrical conductive electrodes, but could optionally be micromachined (MEMS) parallel non-curved or curved surfaces, or further optionally could be non-conductive materials that are coated with a conductive layer. Many types of FAIMS electrode geometry can be used, including domed inner electrodes, side-to-side configurations, parallel plates, and spherical geometry, as some non-limiting examples. The reflective element 446 serves to redirect the laser beam 444 if the beam is passed through the longitudinal axis of a cylindrical inner electrode 456 and out through laser orifice 460. This is practical, for example, if the FAIMS is of the side-to-side geometry. Note also that it is necessary to prevent contamination from entering the gas flow in FAIMS through the laser orifice 460. This can optionally be accomplished by providing a window across the laser orifice 460 through which the laser is directed, or by providing a flow of gas outwards through the laser orifice 460 to carry away potential contaminants.

Still referring to FIG. 8, several optional approaches for directing the laser beam at the sample spot 406 are considered. For example, the laser beam 444 directed through the inner electrode 456 of a cylindrical geometry FAIMS optionally is guided within a flexible optical fiber. The optic fiber passes from a laser source 462, through a coupling to the inner electrode 456 of FAIMS, and a similar optical fiber guides the laser to the opening 460 in the inner electrode 456. The optic fiber terminates with a small lens that focuses the laser beam 444 onto the sample spot 406 on sample target plate 408. 1t s a benefit of this arrangement that the alignment of the laser beam is very simple when using fiber optic connections. It is also a benefit of this system that the focusing of the laser on the sample spot 406 is very simple. Because of the close proximity of the terminus of the fiber optic at opening 408 and the lens used at this point, the strong focus region of the laser beam is quite deep, and therefore the details of the preparation of the sample become less stringent. In other words the sample may have thickness, for example composed of crystals of co-crystallized matrix combined with analyte molecules, but irregardless of this finite thickness of sample, the desorption and ionization (if appropriate) occurs because the laser beam is close to constant flux throughout a thickness that exceeds that of the sample.

For the versions of FAIMS shown in FIGS. 5 to 8 that lack a discrete curtain plate, ion formation occurs in a region that is influenced by the high voltage high frequency asymmetric waveform used to create the electric fields in the analyzer region of FAIMS. In this case, the laser based desorption and ionization process is readily coordinated with the phase of the asymmetric waveform used for separation of the ions in the analyzer region of FAIMS. In other words, the pulse of the laser beam is timed to be synchronized with a selected part of the asymmetric waveform. If the ions are formed in a region close to the analyzer region of FAIMS, it is beneficial that this process occur in conjunction with application of a voltage across the analyzer region that moves the ions of interest away from the target plate surface. In this case, for example, the laser is pulsed during the phase of the waveform that ensures that the electric field moves the ions of interest away from the target plate surface. Since the fields that are established in the analyzer region of FAIMS can be strong, if the ions are formed during a portion of the asymmetric waveform that directs the ions of interest away from the surface, a greater percentage of the ions will be retained within the FAIMS analyzer region. It is also recognized that the pulse of laser beam that creates the ions may also tend to initiate an electrical discharge between the analyzer electrodes of FAIMS. To avoid this problem, optionally the laser desorption/ionization pulse is timed to occur while the electric field between the FAIMS electrodes is not strong but during the increase of voltage, so that the ions formed are quickly directed away from the surface.

Figure 9:
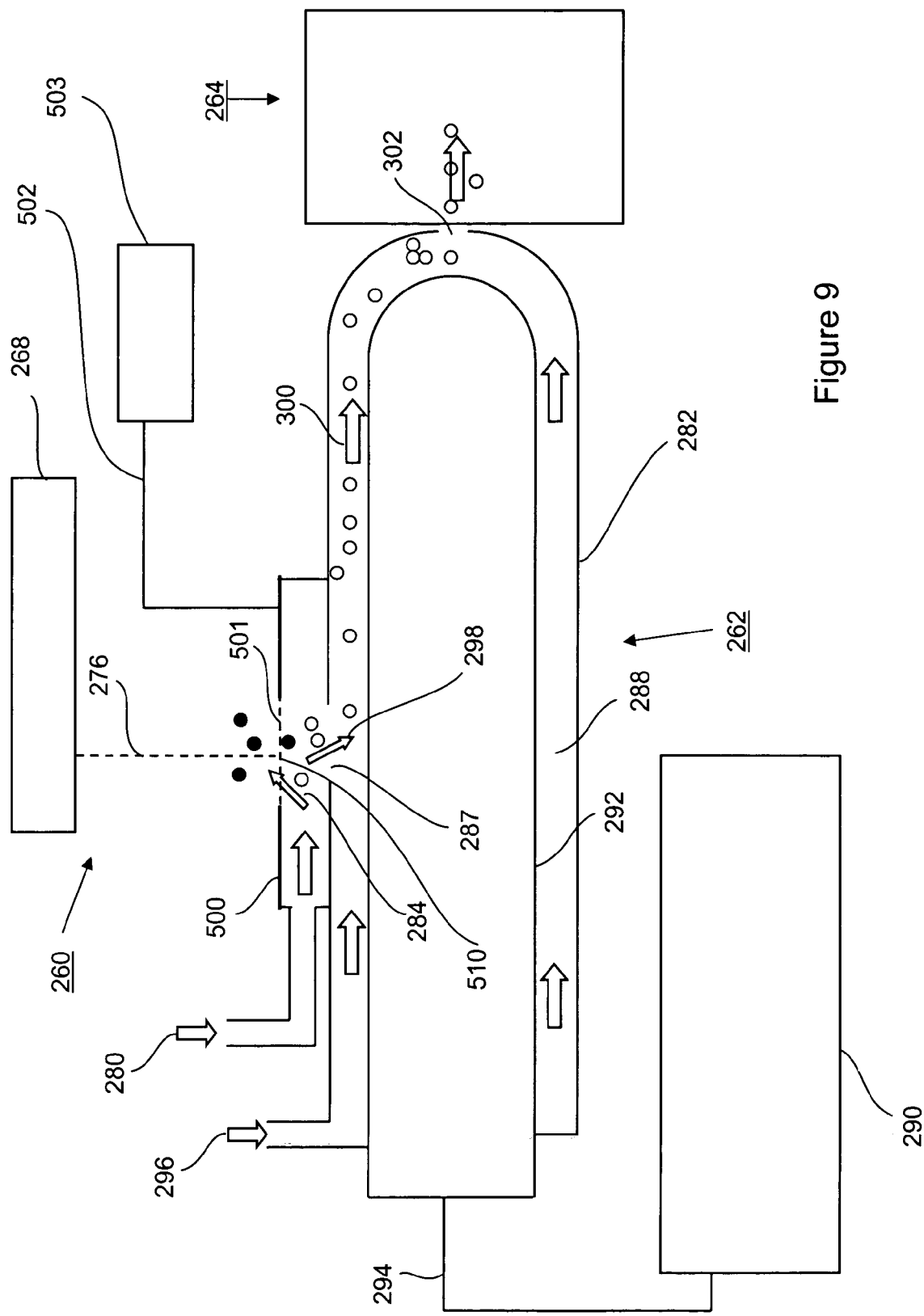
FIG. 9 is a simplified longitudinal cross sectional view of a system according to another embodiment of the instant invention, including an atmospheric pressure MALDI ionization source, a FAIMS, and a detection system.

FIG. 9 is a simplified longitudinal cross sectional view of a system according to an embodiment of the instant invention, including an atmospheric pressure MALDI ionization source 260, a FAIMS 262, and a detection system 264. This figure illustrates a FAIMS system similar to that shown in FIG. 4, but in which the MALDI target plate 266 and the curtain plate 267 of FIG. 4 have been replaced with a modified curtain plate 500 that incorporates a porous region 501 with openings through which a portion of the flow of curtain gas 280 flows to carry away neutral molecules generated by the laser beam 276. Elements labeled with the same numerals have the same function as those illustrated in FIG. 4. A voltage is applied to the modified curtain plate 500 using a power supply 503 through coupling 502.

The apparatus shown at FIG. 9 includes a modified curtain plate 500 that is disposed parallel to and in close proximity to the ion inlet 287 of FAIMS 262. Furthermore, a target region on the porous region 501 of the modified curtain plate 500 is at least partially transparent to light of a wavelength that is provided by a laser source 268. Optionally, the target plate is partly transparent to the laser light. During use, a sample spot 510 is applied to the target region on the porous region 501 of the modified curtain plate 500. In this example, the sample spot 510 is applied to the side of the target region that, in use, faces the ion inlet orifice 287. Preferably, the target region on the porous region 501 of the modified curtain plate 500 is also at least partly conductive so as to maintain the voltages that are applied to the modified curtain plate 500 by power supply 503 via electrical coupling 502, and to minimize electric charging of the target region on the porous region 501 of the modified curtain plate 500 caused by ionization of the sample spot. A laser beam 276 is directed from the laser source 268 to impinge upon or strike a back surface of the target region on the porous region 501 of the modified curtain plate 500. Some of the laser light is transmitted through the porous region 501 and ionizes some of the compounds in the sample spot. The ion cloud that is produced is directed towards the ion inlet 287 of FAIMS by application of voltages to the modified curtain plate 500 and to the outer electrode 282 of FAIMS. A curtain gas flow 280 is provided within the space between the modified curtain plate 500 and an outer electrode 282 of FAIMS. A portion 284 of the curtain gas flow 280 passes outwardly through the porous region 501 of the modified curtain plate 500 and serves to redirect away from the entrance to FAIMS the neutral molecules that are generated by the laser beam 276 striking the sample spot. Some ions pass through the ion inlet orifice 287 into a FAIMS analyzer region 288, in part because of drift imparted by the electric field between the modified curtain plate 500 and the outer electrode 282 of FAIMS. If a portion 298 of the curtain gas flows into the analyzer region 288 between an inner electrode 292 and the outer electrode 282, this gas flow 298 (the analyzer gas portion) also assists in the transfer of ions into FAIMS. The ions are carried through the FAIMS analyzer region 288 by a carrier gas flow composed in part of the analyzer gas portion 298 and an optional additional gas flow 296. The ions in FAIMS are separated by application of DV and CV by power supply 290 connected to the inner electrode 292 of FAIMS via an electrical coupling 294. The voltages applied to the inner electrode 292 create electric fields between the inner electrode 292 and the outer electrode 282 that separate the ions while the ions are transported along the analyzer region 288. The mixture 300 of ions and carrier gas travels to an ion outlet orifice 302 and into the detection system 264. The detection system 264 optionally includes further ion separation technologies including ion mobility, mass spectrometry, or FAIMS, and an ion detector such as for example one of an amperometric, photometric or electron multiplication detector. The distance between the ion inlet 287 and the modified curtain plate 500 is established by optimization of the intensity of signals detected for the ions of interest.

Figure 10:
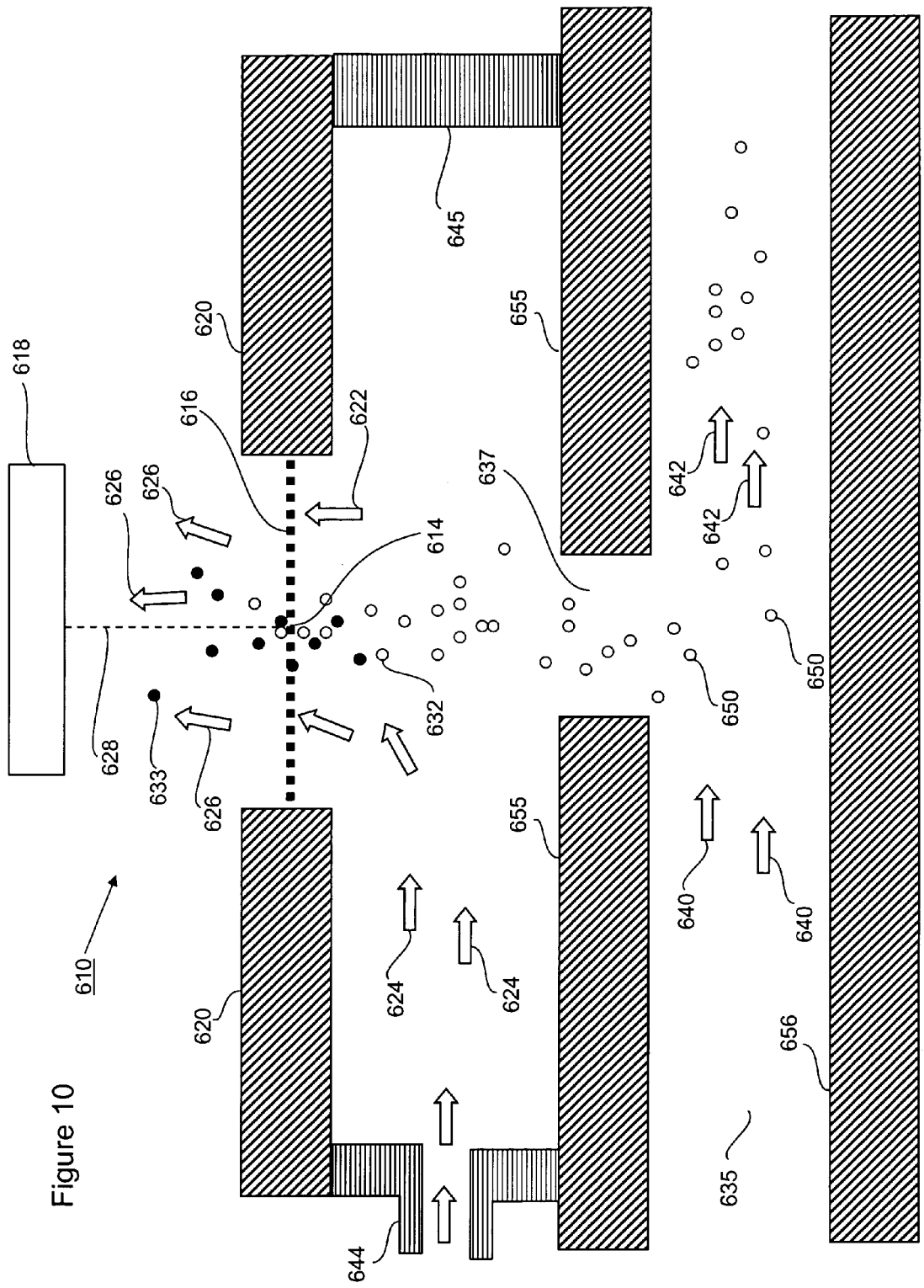
FIG. 10 is an expanded view of the ion inlet region of the system shown at FIG. 9; and, FIG. 11 is a simplified flow diagram of a method of separating ions according to an embodiment of the instant invention.

FIG. 10 illustrates an expanded view of the region of the MALDI target area shown in FIG. 9. The laser beam 628 is directed to strike a porous region 616 of the modified curtain plate 620. The sample is deposited as a sample spot 614 on the porous region 616. The laser beam 628 hits a region on the porous region 614 and generates a cloud of species formed from the sample, including neutral species 633 indicated as filled circles in FIG. 10, and ionized species 632 indicated by open circles. A flow of curtain gas 624 flows into curtain gas inlet 644 that is part of an electrically insulating spacer 645 between the modified curtain plate 620 and the outer electrode 655 of FAIMS. The flow of curtain gas 624 passes outward from between the modified curtain plate 620 and the outer electrode 655 of FAIMS through the porous region 616 of the modified curtain plate 620. Optionally (not shown in this figure) a portion of the curtain gas 624 helps carry ions into the FAIMS analyzer through the FAIMS ion inlet orifice 637. The ions 650 that enter the FAIMS analyzer region 635 are carried along the analyzer region 635 by the flow of carrier gas 642 and are separated by FAIMS based on their compound-dependent ion mobility properties. Neutral species 633 that are formed when the laser beam 628 hits the sample spot 614 are dispersed in the region of this laser impact, but are then carried away from the FAIMS by the curtain gas flow 624 that passes through the porous region 616 of the modified curtain plate 620. The exit gas 626 has passed through the porous region 616 and is carrying most of the neutral species 633 away from FAIMS. Optionally, the porous region 616 shown at FIG. 10 is spaced slightly apart from the modified curtain plate, in an arrangement that is similar to the ones shown at FIG. 6b or FIG. 6c.

Still referring to FIG. 10, it is beneficial that the flow of curtain gas 624 ensures that the neutral species 633 formed when the laser beam 628 strikes the sample spot 614 do not enter the analyzer region 635. It is an advantage of the device shown in FIG. 10 that although the neutral species 633 may be initially dispersed by the energy of the laser beam into a space around the vicinity of the sample spot 614, the flow of curtain gas 624 near the sample spot 614 is flowing in a direction substantially away from the FAIMS ion inlet 637.

Figure 11:
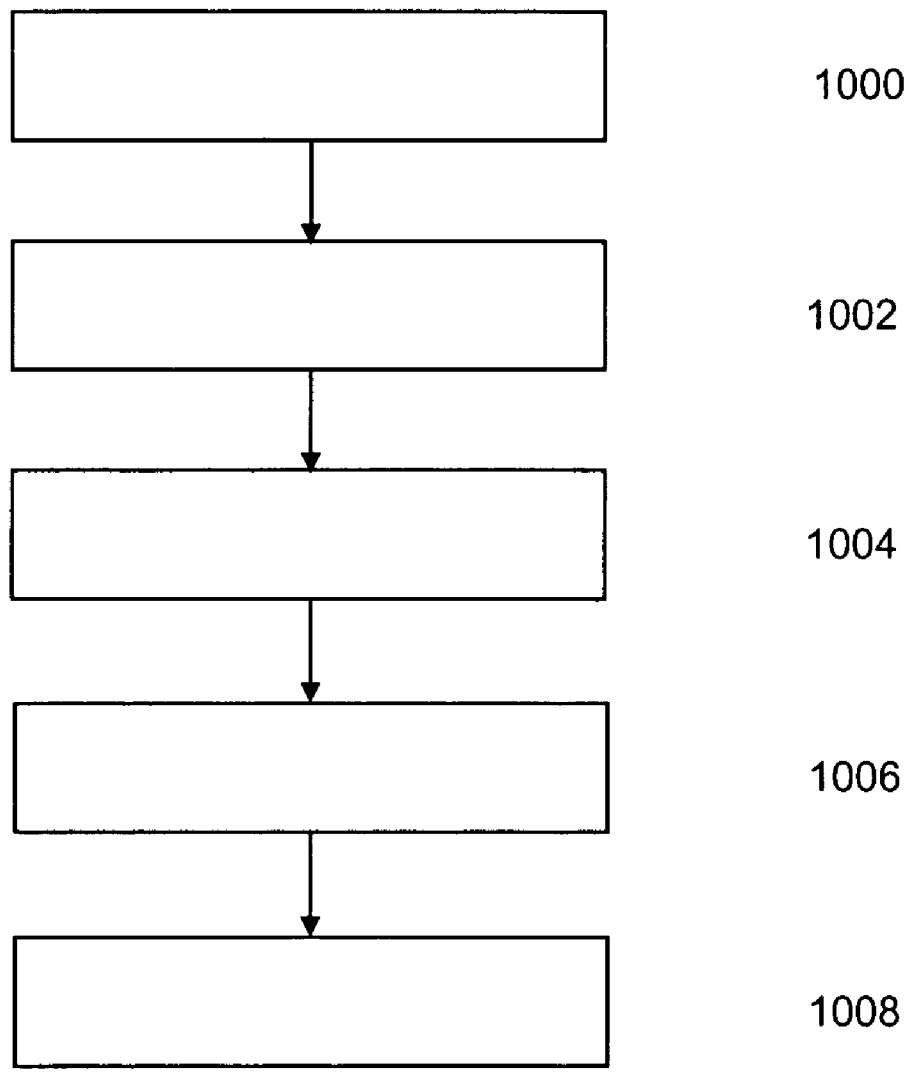

Referring now to FIG. 11, shown is a method of separating ions according to an embodiment of the instant invention. At step 1000, a spot of a sample material is applied to a target plate. At step 1002, the target plate is mounted in fluid communication with an ion inlet orifice of a FAIMS analyzer region and externally to the FAIMS analyzer region. Using a laser light source that is disposed external to the FAIMS analyzer region, the target plate is irradiated at step 1004 with light of a predetermined wavelength, the light of a predetermined wavelength being selected to affect the sample material applied to the target plate so as to produce ions of the sample material. At step 1006, the ions of the sample material are directed along an ion flow path between the target plate and FAIMS analyzer region, via the ion inlet orifice. At step 1008, a flow of a gas is directed countercurrent to the ion flow path, and passing through the target plate. The numbering of the steps is not intended to imply any particular order of the steps. For instance, optionally step 1002 is performed to mount the target plate prior to performing step 1000 to apply a spot of a sample material to the target plate. Similarly, optionally step 1008 is performed to provide the flow of a gas through the target plate simultaneously with each one or only some of steps 1000, 1002, and 1004. Advantageously, the outward flow of gas through the target plate assists in desolvation of ions and directs neutral molecules away from the FAIMS analyzer region.

Numerous other embodiments may be envisaged without departing from the spirit and scope of the invention.

What is claimed is:

1. An apparatus comprising:
   a FAIMS analyzer for separating ions of a sample material and comprising an electrode having a first side and a second side that is opposite the first side, the first side of the electrode defining a boundary of a first region and the second side of the electrode defining a boundary of a second region;
   a gas inlet for providing a flow of a gas within the first region;
   an orifice having a periphery and being defined within a portion of the electrode for providing fluid communication between the first region and the second region; and,
   a laser-based ionization source for producing the ions of a sample material and comprising:
   a target plate disposed adjacent to the second side of the electrode and in an aligned relationship with the orifice, the target plate having a front surface for supporting the sample material thereon and having a back surface opposite the front surface, the target plate disposed for supporting a flow of the gas, via the orifice, in a direction from the first region to the second region; and, laser light source in optical communication with the target plate for irradiating the sample material supported thereon with light of a predetermined wavelength, for producing the ions from the sample material.

2. An apparatus according to claim 1, wherein the first region is a FAIMS analyzer region defined by a space between a first FAIMS electrode and a second FAIMS electrode, and wherein the electrode defining the orifice is the first FAIMS electrode.

3. An apparatus according to claim 2, wherein the orifice comprises an ion inlet orifice for introducing the ions of a sample material into the FAIMS analyzer region.

4. An apparatus according to claim 1, wherein the first region is a curtain gas region defined by a space between a curtain electrode and a first FAIMS electrode, and wherein the electrode defining the orifice is the curtain electrode.

5. An apparatus according to claim 4, comprising an ion inlet orifice defined within a portion of the first FAIMS electrode, the ion inlet orifice in fluid communication with the orifice.

6. An apparatus according to claim 1, wherein the target plate is at least partly porous for supporting a flow of the gas therethrough.

7. An apparatus according to claim 6, wherein the target plate forms a gas-tight seal with the electrode about the periphery of the orifice.

8. An apparatus according to claim 6, wherein the target plate is spaced apart from the electrode to define a gap between the target plate and the periphery of the orifice.

9. An apparatus according to claim 1, wherein the target plate comprises an electrically conductive material.

10. An apparatus according to claim 1, wherein the target plate is at least partially transmissive to the light of a predetermined wavelength and wherein the laser light source is disposed for irradiating the back surface of the target plate.

11. An apparatus according to claim 2, comprising a laser orifice defined within the second FAIMS electrode, wherein the laser light source is disposed for launching the light of a predetermined wavelength along an optical path including the laser orifice and the orifice, for irradiating the front surface of the target plate.

12. An apparatus according to claim 5, comprising a second FAIMS electrode, the second FAIMS electrode spaced apart from the first FAIMS electrode, a space between the first FAIMS electrode and the second FAIMS electrode defining a FAIMS analyzer region.

13. An apparatus according to claim 12, comprising a laser orifice defined within the second FAIMS electrode, wherein the laser light source is disposed for launching the light of a predetermined wavelength along an optical path including the laser orifice, the ion inlet orifice, and the orifice, for irradiating the front surface of the target plate.

14. An apparatus comprising:
a FAIMS analyzer comprising a first electrode and a second electrode that is disposed in a spaced-apart relationship with the first electrode, a space between the first electrode and the second electrode defining a FAIMS analyzer region for separating ions of a sample material;
an ion inlet orifice having a periphery and being defined within the first electrode; and,
a laser-based ionization source for producing ions from a sample material and comprising:

a target plate disposed adjacent to the ion inlet orifice and having a thickness, the target plate having a front surface for supporting the sample material thereon and having a back surface opposite the front surface, the target plate disposed for supporting a flow of a gas therethrough outwardly from the FAIMS analyzer region via the ion inlet orifice; and, a laser light source disposed external to the FAIMS analyzer region and in optical communication with the target plate for irradiating the sample material supported on the target plate with light of a predetermined wavelength, for producing the ions from the sample material.

15. An apparatus according to claim 14, wherein the target plate forms a gas-tight seal with the first electrode about the periphery of the ion inlet orifice.

16. An apparatus according to claim 14, wherein the target plate comprises an electrically conductive material.

17. An apparatus according to claim 16, wherein the target plate comprises a metallic mesh.

18. An apparatus according to claim 16, wherein the target plate is at least partly porous.

19. An apparatus according to claim 14, wherein the target plate is disposed external to the analyzer region with the front surface in a facing relationship with the inlet orifice.

20. An apparatus according to claim 19, wherein the target plate is at least partially transmissive to the light of a predetermined wavelength and wherein the laser light source is disposed for irradiating the back surface of the target plate.

21. An apparatus according to claim 19, comprising a laser orifice defined within the second electrode, wherein the laser light source is disposed for launching the light of a predetermined wavelength along an optical path including the laser orifice and the ion inlet orifice, for irradiating the front surface of the target plate.

22. An apparatus according to claim 21, wherein the optical path is a folded optical path including a reflective surface.

23. An apparatus according to claim 14, wherein the target plate is removably mounted to the first electrode along a portion of the first electrode including the inlet orifice.

24. An apparatus according to claim 23, wherein the target plate comprises a mesh-material.

25. An apparatus according to claim 24, wherein the target plate comprises a mesh of an electrically conductive material.

26. An apparatus according to claim 25, wherein the electrically conductive material is selected from the group consisting of: a metal; and, an electrically conducting synthetic polymer.

27. A method of separating ions, comprising:
applying a spot of a sample material to a target plate;
mounting the target plate in fluid communication with an ion inlet orifice of a FAIMS analyzer region and externally to the FAIMS analyzer region;
using a laser light source that is disposed external to the FAIMS analyzer region, irradiating the target plate with light of a predetermined wavelength, the light of a predetermined wavelength selected to affect the sample material applied to the target plate so as to produce ions of the sample material;
directing the ions of the sample material along an ion flow path between the target plate and FAIMS analyzer region, via the ion inlet orifice; and, directing a flow of a gas counter-current to the ion flow path and passing through the target plate.

28. A method according to claim 27, wherein irradiating the target plate comprises launching the light of a predetermined wavelength along an optical path toward a back surface of the target plate.

29. A method according to claim 28, comprising providing a target plate that is at least one of partly transmissive to the light of a predetermined wavelength and partially transmissive to the light of a predetermined wavelength.

30. A method according to claim 27, wherein irradiating the target plate comprises launching the light of a predetermined wavelength along an optical path that passes through a portion of the FAIMS analyzer region and outwardly through the ion inlet orifice to impinge upon a front surface of the target plate.

31. A method according to claim 30, wherein the laser light source is disposed on a side of the FAIMS analyzer region opposite the target plate.

32. A method according to claim 30, wherein the optical path includes a reflective surface and wherein irradiating the target plate comprises reflecting the light of a predetermined wavelength from the reflective surface.

* * * * *